US011059919B2

United States Patent
Milan et al.

(10) Patent No.: US 11,059,919 B2
(45) Date of Patent: Jul. 13, 2021

(54) POLYMERS FROM MUCONIC ACID ISOMERS AND ITS DERIVATIVES

(71) Applicant: PTT GLOBAL CHEMICAL PUBLIC COMPANY LIMITED, Bangkok (TH)

(72) Inventors: Jay L. Milan, Natick, MA (US); Michael Mang, Bainbridge, GA (US); Cenan Ozmeral, Charlotte, NC (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 0 days.

(21) Appl. No.: 15/522,123

(22) PCT Filed: Oct. 23, 2015

(86) PCT No.: PCT/US2015/057188
§ 371 (c)(1),
(2) Date: Apr. 26, 2017

(87) PCT Pub. No.: WO2016/069411
PCT Pub. Date: May 6, 2016

(65) Prior Publication Data
US 2017/0335031 A1    Nov. 23, 2017

Related U.S. Application Data

(60) Provisional application No. 62/069,613, filed on Oct. 28, 2014.

(51) Int. Cl.
C08G 63/00    (2006.01)
C08F 122/14   (2006.01)
(Continued)

(52) U.S. Cl.
CPC .......... *C08F 122/14* (2013.01); *C07C 29/149* (2013.01); *C07C 51/353* (2013.01);
(Continued)

(58) Field of Classification Search
None
See application file for complete search history.

(56) References Cited

U.S. PATENT DOCUMENTS 5,616,496 A * 4/1997 Frost .................... C12N 9/0069
435/142
9,969,669 B2 * 5/2018 Asikainen ............... C07C 67/08
(Continued)

FOREIGN PATENT DOCUMENTS

WO    WO-2010085712 A2 * 7/2010 ........... C07C 69/593

OTHER PUBLICATIONS

Xie et al. "Biotechnological production of muconic acid: current status and future prospects" Biotechnology Advances 32, 2014, 615-622. (Year: 2014).*

(Continued)

*Primary Examiner* — Robert S Loewe
(74) *Attorney, Agent, or Firm* — Oblon, McClelland, Maier & Neustadt, L.L.P.

(57) ABSTRACT

This invention relates to polymerization of muconic acid and its derivatives. Muconic acid useful for the invention can be in any of its isomeric forms including cis, cis-muconic acid (ccMA), cis, trans-muconic acid (ctMA), and trans, trans-muconic acid (ttMA). Muconic acid used in the invention can be derived either from renewable carbon resources through biological fermentation or from non-renewable petrochemical resources through biological fermentation or chemical conversion.

4 Claims, 12 Drawing Sheets

(51) Int. Cl.

| | |
|---|---|
| C08G 63/52 | (2006.01) |
| C08G 63/08 | (2006.01) |
| C08F 220/06 | (2006.01) |
| C07C 67/327 | (2006.01) |
| C07C 67/303 | (2006.01) |
| C07C 67/343 | (2006.01) |
| C07C 51/353 | (2006.01) |
| C07C 51/36 | (2006.01) |
| C07C 67/333 | (2006.01) |
| C08F 136/14 | (2006.01) |
| C07C 51/377 | (2006.01) |
| C08F 236/14 | (2006.01) |
| C07C 29/149 | (2006.01) |
| C07C 69/753 | (2006.01) |
| C07C 69/82 | (2006.01) |
| C08F 267/06 | (2006.01) |
| C08F 283/01 | (2006.01) |
| C08F 283/04 | (2006.01) |
| C08G 63/688 | (2006.01) |
| C08G 69/00 | (2006.01) |

(52) U.S. Cl.
CPC ............ *C07C 51/36* (2013.01); *C07C 51/377* (2013.01); *C07C 67/303* (2013.01); *C07C 67/327* (2013.01); *C07C 67/333* (2013.01); *C07C 67/343* (2013.01); *C07C 69/753* (2013.01); *C07C 69/82* (2013.01); *C08F 136/14* (2013.01); *C08F 220/06* (2013.01); *C08F 236/14* (2013.01); *C08F 267/06* (2013.01); *C08F 283/01* (2013.01); *C08F 283/045* (2013.01); *C08G 63/00* (2013.01); *C08G 63/08* (2013.01); *C08G 63/52* (2013.01); *C08G 63/688* (2013.01); *C08G 69/00* (2013.01); *C07C 2601/14* (2017.05); *C07C 2601/16* (2017.05)

(56) References Cited

U.S. PATENT DOCUMENTS

2010/0314243 A1* 12/2010 Frost ................. C07C 67/08
  204/157.15
2013/0085255 A1*  4/2013 Coudray .............. C07C 255/09
  528/319

OTHER PUBLICATIONS

Lin et al. "Extending shikimate pathway for the production of muconic acid and its precursor salicylic acid in *Escherichia coli*" Metabolic Engineering 23, 2014, 62-69. (Year: 2014).*

Bando et al. "Radical Polymerization of Muconic Acid and Ethyl Muconate" Journal of Polymer Science: Polymer Chemistry Edition, vol. 15, 1977, 1917-1926. (Year: 1977).*

Matsumoto et al. "Stereospecific Polymerization of Dialkyl Muconates through Free Radical Polymerization: Isotropic Polymerization and Topochemical Polymerization" Macromolecules, 1996, 29, 423-432. (Year: 1996).*

\* cited by examiner n= 0 – 10, Saturated, unsarturated, aromatic, aliphatic, hetreoaromatic diamines

POLYMERS FROM MUCONIC ACID ISOMERS AND ITS DERIVATIVES

CROSS-REFERENCE TO RELATED APPLICATION

The application is the U.S. national stage application of International Patent Application No. PCT/US2015/057188, filed on Oct. 23, 2015 which claims the priority of the U.S. Provisional Application Ser. No. 62/069,613 filed on Oct. 28, 2014.

This application claims the priority of the U.S. Provisional Application Ser. No. 62/069,613, filed on Oct. 28, 2014.

FIELD OF THE INVENTION

The present invention is in the field of producing specialty and commodity muconic acid polymers. More specifically, the present invention is related to the conversion of muconic acid isomers and its derivatives into homopolymers, condensation polymers, ring opening polymers and copolymers.

BACKGROUND OF THE INVENTION

There has been a growing interest in manufacturing specialty chemicals using renewable biological materials as feedstock. For examples, biocatalysts have been developed to manufacture succinic acid, muconic acid, lactic acid, 3-hydroxypropionic acid, 1,3-propanediol, 1.4-butanediol and butanol using biological feedstock such as glucose, glycerol and sucrose. These specialty chemicals derived from biological materials can be used in a number chemical and polymer industries to develop materials with unique properties. These materials may have properties close to the materials derived from petrochemical feedstock and therefore these biomass-derived materials could be used to avoid our dependence on fossil fuels. The present invention is related to the production of muconic acid using renewable biological materials as feedstock and its application in the manufacture of polymers.

Since there is no chemical difference between the muconic acid derived from renewable biological materials and the muconic acid derived from petrochemical feedstock other than the C14/C12 ratio, the method of manufacturing polymers according to the present invention can be practised using either the muconic acid derived from renewable biological materials or muconic acid derived from petrochemical feedstock. In preferred embodiments of the present invention, it is desirable to use muconic acid and it derivatives obtained from renewable biological feedstock using fermentation process.

A number of biocatalysts for the production of muconic acid as well as a number of processes for fermentative production of muconic acid have been developed and efforts are being made to manufacture biomass-derived muconic acid in commercial scale. The biocatalysts can be derived either from bacterial or fungal species including yeast strains. Any one of those biocatalysts and the processes for the fermentative production of muconic acid can be followed to obtain muconic acid useful as a raw material for the chemical processes described in the present invention.

SUMMARY OF THE INVENTION

This present invention provides a process for polymerization of muconic acid isomers and its derivatives including aliphatic esters, aromatic esters, alkyl aromatic esters and aromatic alkyl esters of muconic acid through one or more chemical reaction pathways and in some cases, in combination with other suitable monomers. Also provided in this invention are methods for derivatizing muconic acid into one or other monomers such as 3,4-disulfohexanedioic acid and 2,3,4,5 tetrahalohexanedioic acid through simple chemical reactions. The resulting muconic acid derivatives including alkyl, aryl, alkyl aromatic and aromatic alkyl esters of muconic acid can be polymerized by itself or in combination with other suitable monomers. Muconic acid suitable for this invention is preferably obtained from renewable biomass resources through fermentation or from non-renewable petrochemical feedstock through chemical catalytic processes or biological conversion.

In one embodiment of the present invention homopolymers are derived from isomers of muconic acid or its derivatives including aliphatic esters, aromatic esters, alkyl aromatic esters and aromatic alkyl esters of muconic acid. In one aspect of this embodiment, the monomeric muconic acid or its derivative is selected from a group consisting of EZ isomer, ZZ isomer, EE isomer and ZE isomer. In another aspect of this embodiment, the present invention provides homopolymers derived from muconic acid or its derivatives further comprising one or more monomers selected from a group consisting of butadiene, isoprene, methaacrylic acid, styrene, ethylene, propylene, acrylic acid and acrylonitrile.

In another embodiment, the present invention provides homopolymers derived from one or more monomers selected from a group consisting of butadiene, isoprene, methaacrylic acid, styrene, ethylene, propylene, acrylic acid and acrylonitrile further comprising muconic acid monomers or one of its derivatives including aliphatic esters, aromatic esters, alkyl aromatic esters and aromatic alkyl esters of muconic acid as cross-linkers. The muconic acid monomers and its derivatives including aliphatic esters, aromatic esters, alkyl aromatic esters and aromatic alkyl esters of muconic acid used as cross-linkers according to the present invention are selected from a group consisting of EZ isomer, ZZ isomer, EE isomer and ZE isomer.

In yet another embodiment of the present invention, a ring opening polymerization reaction involving ZZ isomer of muconic acid is provided. In the first step of this ring opening polymerization reaction, ZZ isomer of muconic acid is subjected to lactonization reaction to yield mucono bis-lactone which in turn is subjected to ring opening polymerization reaction to yield a muconic acid polymer.

In another embodiment of the present invention, a polymeric process for the production of condensation polymers is provided. In one aspect of this embodiment, muconic acid or its derivative is subjected to a condensation reaction with a diol leading to the production of muconic polyester. Muconic acid derivatives useful in this condensation reaction include aliphatic esters, aromatic esters, alkyl aromatic esters and aromatic alkyl esters of muconic acid. Diols useful in this condensation reaction process is selected from a group consisting of saturated or unsaturated aliphatic diols, aromatic diols, alkyl aromatic diol and aromatic alkyl diols. In one aspect, this embodiment of the present invention provides polymers derived from the condensation of muconic acid or its derivatives with a diol further comprising one or more monomers selected from a group consisting of butadiene, isoprene, methaacrylic acid, styrene, ethylene, propylene, acrylic acid and acrylonitrile.

In yet another embodiment of the present invention, muconic acid or its derivative is subjected to a condensation reaction with diamines leading to the production of muconic polyamide. Muconic acid derivatives useful in this condensation reaction include aliphatic, aromatic, alkyl aromatic and aromatic alkyl esters of muconic acid. Diamines useful in this condensation reaction include saturated or unsaturated aliphatic diamines, aromatic diamines, alkyl aromatic diamines and aromatic alkyl diamines. In one aspect, this embodiment of the present invention provides polymers derived from the condensation of muconic acid or its derivatives with a diamine further comprising one or more monomers selected from a group consisting of butadiene, isoprene, methaacrylic acid, styrene, ethylene, propylene, acrylic acid and acrylonitrile.

In yet another embodiment of the present invention, a polymeric process for the synthesis of cross-linked polymers is provided. In one aspect of the present invention, the unsaturated double bonds in muconic acid homopolymers and muconic acid condensation polymers are used to cross-link these polymers with other monomers selected from a group consisting of acrylic acid, acrylonitrile, styrene, ethylene, methacrylic acid, propylene, butadiene and isoprene. In another aspect of this invention, muconic acid monomers and its derivatives are used as cross-linkers to alter or modify the properties of the traditional homopolymers such as polyacrylic acid, polyacrylonitrile, polystyrene, polyethylene, polymethaacrylic acid, polypropylene, polybutadiene and polyisoprene.

In yet another embodiment of the present invention, a chemical process for the production of hex-3-enedioic acid is provided. In the first step of this chemical conversion process, muconic acid or its derivative, including aliphatic esters, aromatic esters, alkyl aromatic esters and aromatic alkyl esters of muconic acid, is subjected to an electrolysis reaction using electrolyte, anode, cathode and electricity applied to the medium leading to the production of hex-3-enedioic acid. Hex-3-enedioic acid is used in polymeric applications such as condensation polymerization, cross-linked polymerization or copolymerization. In one aspect of this embodiment, hex-3-enedioic acid resulting from electrolytic reaction of muconic acid is further reacted with an aldehyde or a ketone under condition leading to the production of 2, 5 dimethylene-3-enedioic acid. 2, 5 dimethylene-3-enedioic acid or its derivatives is used in polymeric applications and adhesives related applications. In another aspect of this embodiment, 2, 5 dimethylene-3-enedioic acid is cyclized and hydrogenated to produce cyclohexane dicarboxylic acid (CHDA) derivatives or oxidized to yield terepthalic acid derivatives.

In yet another embodiment of the present invention, a chemical process for the production of 3,4-disulfohexanedioic acid is provided. In this chemical conversion process, muconic acid or its derivative, including aliphatic esters, aromatic esters, alkyl aromatic esters and aromatic alkyl esters of muconic acid, is subjected to an sulfonation reactions using sulfonating reagents such as sodium sulfite, sodium thiosulfate and sulfurdioxide leading to the production of 3,4-disulfohexanedioic acid. 3,4-disulfohexanedioic acid or its derivative, including aliphatic esters, aromatic esters, alkyl aromatic esters and aromatic alkyl esters is used in surfactants related applications. 3,4-disulfohexanedioic acid is also polymerized with diols and diamines to produce 3,4-disulfohexanedioic polyester or 3,4-disulfohexanedioic polyamide. Polyesters and polyamides derived from 3,4-disulfohexanedioic acid is useful as a surface modifying products such as flocculants or coagulants. Polyesters and polyamides derived from 3,4-disulfohexanedioic acid are also used in ion-exchange resins or proton exchange resins to modify acidic and basic properties of the reaction mixtures.

In yet another embodiment of the present invention, a chemical process for the production of 2,3,4,5-tetrabromohexanedioic acid is provided. In this chemical conversion process, muconic acid or its derivative, including aliphatic esters, aromatic esters, alkyl aromatic esters and aromatic alkyl esters of muconic acid, is subjected to an bromination reactions using bromine under organic or aqueous solvent system leading to the production of 2,3,4,5-tetrabromohexanedioic acid. Other halogens such as chlorine, iodine and fluorine are also used for the synthesis of 2,3,4,5-tetrahalohexanedioic acid or its derivative, including aliphatic esters, aromatic esters, alkyl aromatic esters and aromatic alkyl esters. 2,3,4,5-tetrahalohexanedioic acid and its derivatives are also polymerized with diols and diamines to produce 2,3,4,5-tetrahalohexanedioic polyester or 2,3,4,5-tetrahalohexanedioic polyamide. Polyesters and polyamides derived from 2,3,4,5-tetrahalohexanedioic acid is useful in making polymeric products and materials for the production of fire prevention appliances, electronic equipments, fibers, garments and covers for electrical appliances. Polyesters and polyamides derived from 2,3,4,5-tetrahalohexanedioic acid are also used for its extreme water repellent properties. Material surfaces coated or modified with 2,3,4,5-tetrahalohexanedioic acid based polyesters and polyamides are capable of preventing water permeation through capillary forces and are useful in under-water electrical related applications.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations and equivalents in form and function, as will occur to those skilled in the art and having the benefit of this disclosure.

DETAILED DESCRIPTION OF THE PREFERRED EMBODIMENTS

Figure 1:
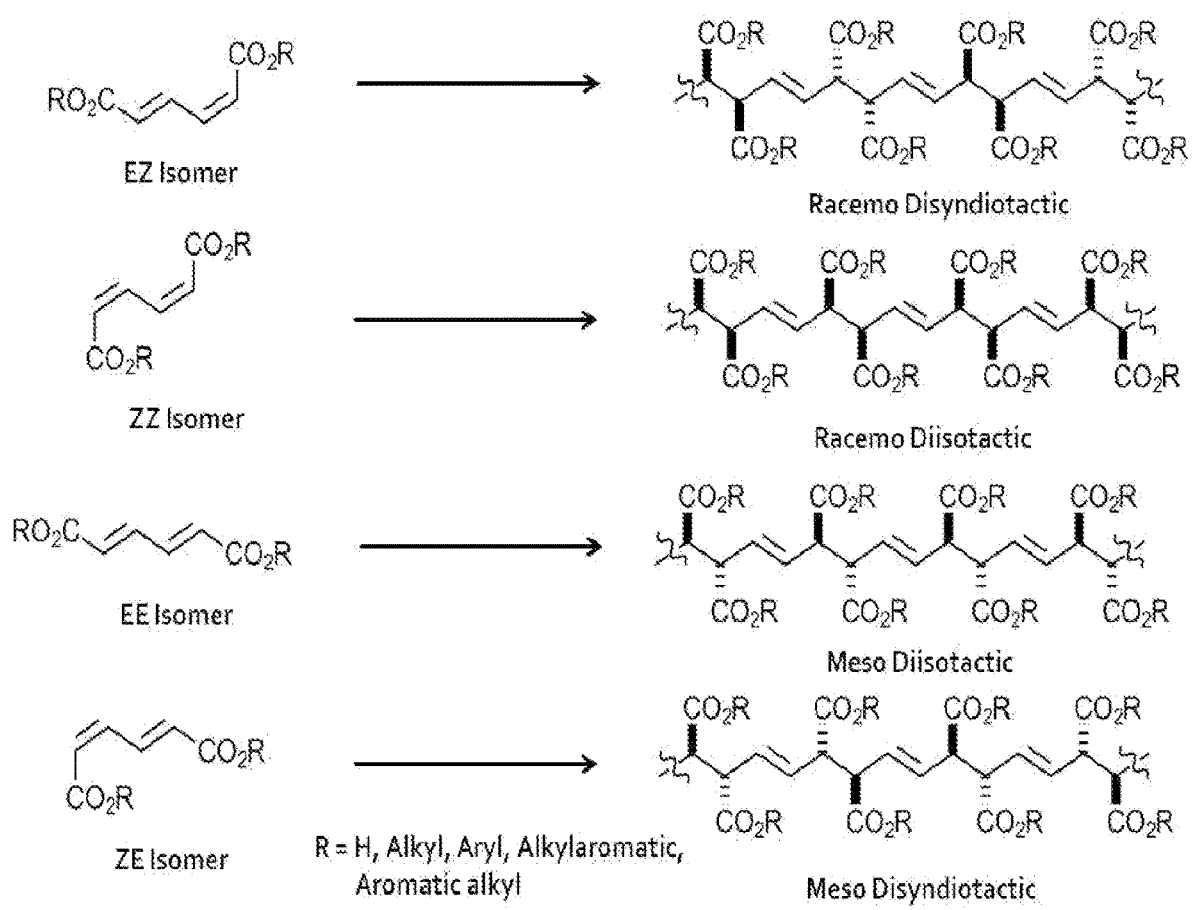
FIG. 1. Homopolymerization of muconic monomers. The muconic monomer suitable for homopolymerization process includes muconic acid and its derivatives including aliphatic esters, aromatic esters, alkyl aromatic esters and aromatic alkyl esters of muconic acid. Either a single isomeric form of muconic monomer or a mixture of isomers of muconic monomers including EZ isomer, ZE isomer, EE isomer and ZZ isomer can be used in the homopolymerization process. Muconic monomers useful for the present invention are derived either from renewable biomass materials through biological fermentation or from petrochemical feedstock through chemical or biological conversion. Muconic monomers are subjected to homopolymerization reaction to yield diastereomerically pure diisotactic or disyndiotactic based homopolymers or mixture of diastereomeric products.
Figure 2:
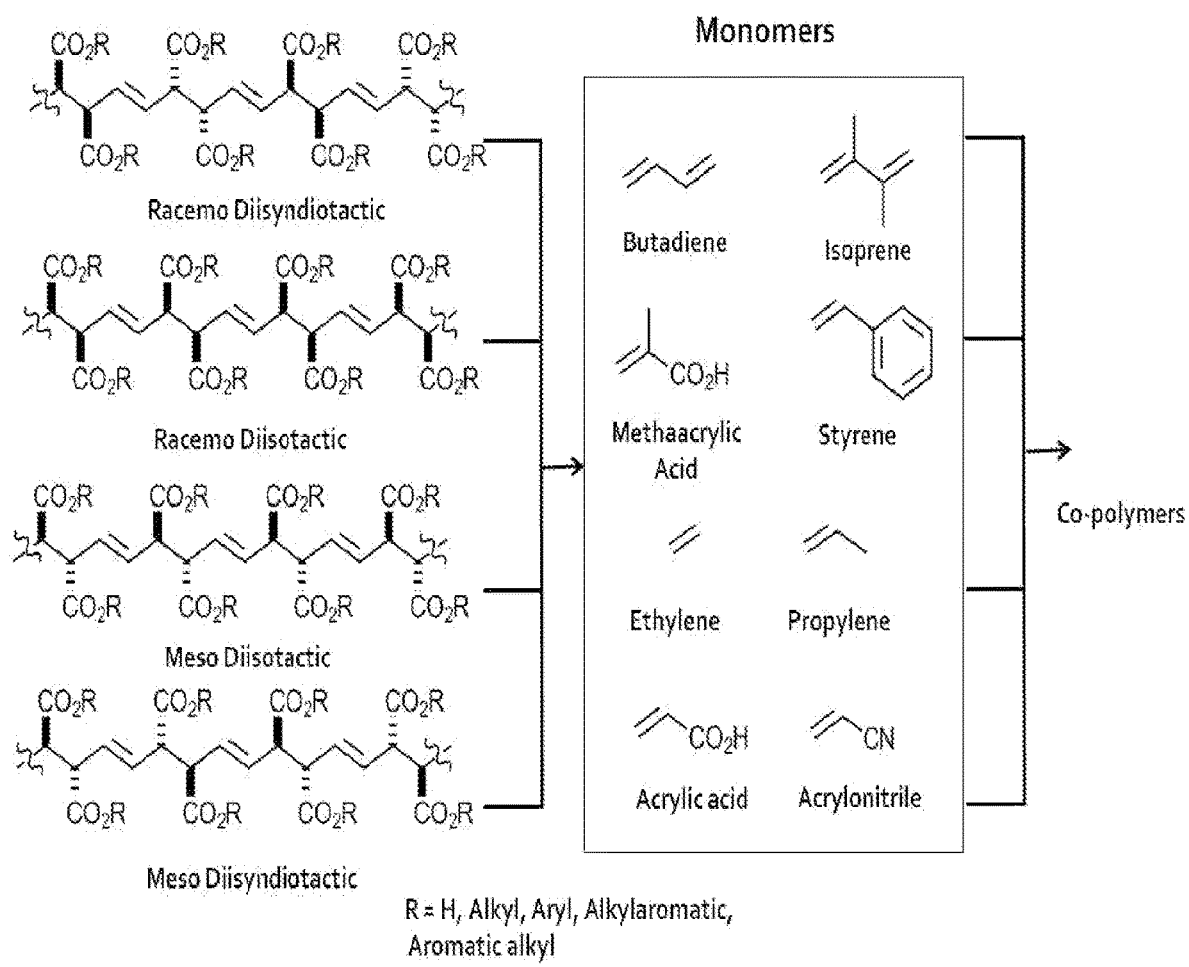
FIG. 2 Preparation of copolymers comprising muconic homopolymers based on muconic acid and its derivatives and conventional polymers based on monomers selected from a group consisting of butadiene, isoprene, acrylic acid, methaacrylic acid, styrene, acrylonitrile, ethylene and propylene. The individual polymers are prepared separately and are physically mixed together to yield a copolymer. The muconic monomers as well as the monomers useful in the preparation of conventional polymers are derived either from renewable biomass resources through fermentation or from non-renewable petrochemical feedstock through chemical catalytic processes or biological conversion.

The present invention provides novel methods for using muconic acid and its derivatives in the preparation of one or other types of polymers such as homopolymers, condensation polymers including polyesters and polyamides, crosslinked polymers, copolymers and polymers resulting from ring-opening polymerization reaction.

Muconic acid useful in the present invention is derived either from renewable biological resources through microbial fermentation or from petrochemical feedstock either via chemical or biological conversion. For example, benzoic acid, catechol, PCA, skimic acid or other petrochemical or biochemical feedstock can be used as a substrate in the biological process leading to the production of muconic acid isomers. It is preferable to use the muconic acid obtained from renewable biological resources. Various derivative of muconic acid including alkyl, aryl, alkylaromatic and aromatic alkyl esters of muconic acid are obtained from muconic acid through one or other chemical reactions. Muconic acid can also be subjected to sulfonation reaction to yield 3,4-disulfohexanedioic acid. Similarly muconic acid can be subjected to halogenation reaction to yield 2,3,4,5-tetrahalohexanedioic acid. Muconic acid, its ester derivatives including alkyl, aryl, alkylaromatic and aromatic alkyl esters of muconic acid, 3,4-disulfohexanedioic acid, 2,3,4, 5-tetrahalohexanedioic acid, hex-3-enedioic acid and 2, 5 dimethylene-3-enedioic acid are referred as monomer useful in the preparation of one or other polymers according to the present invention. The properties of various muconic polymers derived from renewable biological materials are expected to be identical or very similar to those of polymers derived from nonrenewable petrochemical feedstock.

As defined in this invention, renewable biological material includes any feedstock derived from plant materials as opposed to the materials derived from petrochemical feedstock. The term "renewable biological material" is also used interchangeably with the term "biomass". The term "biomass" as used in the present invention refers to carbohydrates, sugars, glycerol and lignocellulosic materials derived from renewable plant resources which can be used in the fermentative production of muconic acid. Muconic acid and its derivatives obtained from renewable biological materials are referred as "biomass-derived". On the other hand muconic acid and its derivatives obtained from petrochemical feedstock are referred as "petrochemical-derived".

The bio-based muconic acid manufactured according to the present invention can be distinguished from muconic acid manufactured following the traditional methods involving petroleum feedstock on the basis of their carbon 14 content following the method ASTM-D6866 provided by American Society of Testing and Materials. Cosmic radiation produces $^{14}C$ ("radiocarbon") in the stratosphere by neutron bombardment of nitrogen. $^{14}C$ atoms combine with oxygen atom in the atmosphere to form heavy $^{14}CO_2$, which, except in the radioactive decay, is indistinguishable from the ordinary carbon dioxide. $CO_2$ concentration and the $^{14}C/^{12}C$ ratio is homogeneous over the globe and because it is used by the plants, the ratio $^{14}C/^{12}C$ is retained by the biomass while the content of $^{14}C$ in the fossil materials, originally derived from photosynthetic energy conversion, has decayed due to its short half-life of 5730 years. By means of analyzing the ratio of $^{14}C$ to $^{12}C$, it is possible to determine the ratio of fossil fuel derived carbon to biomass-derived carbon. International Patent Application Publication No. WO2009/155085 A2 and U.S. Pat. No. 6,428,767 provide details about the use of ASTM-D6866 method for determining percent of biomass-derived carbon content in a chemical composition. The details related carbon dating disclosed in the U.S. Pat. No. 6,428,767 is incorporated herein by reference. An application note from Perkin Elmer entitled "Differentiation between Fossil and Biofuels by Liquid Scintillation Beta Spectrometry—Direct Method" provides details about the methods involving ASTM Standard D6866.

In preferred embodiments, the present invention makes use of the muconic acid produced using one or other microbial strains. Current efforts towards microbial production of muconic acid can be grouped under three categories namely: (1) An aromatic degradation pathway for muconic acid production, in which various aromatic compounds are fed, and the benzene ring portion of aromatic compounds are oxidatively cleaved open; (2) A muconate buildup pathway, in which the muconic acid backbone is built up from various C2, C3, C4, compounds or lysine; and (3) An aromatic amino acid biosynthetic muconic acid pathway, in which muconic acid is built from 3-dehydroshikimate, an intermediate in the aromatic amino acid biosynthetic pathway in many organisms.

Many microorganisms are capable of degrading aromatic compounds containing a benzene ring, such as phenol, catechol, and benzoic acid, using pathways that cleave the aromatic ring to give terminal or intermediate compounds that are non-aromatic compounds such as cis, cis-muconic acid, or 3-carboxy-cis, cis-muconic acid (Niu et al., 2002; Perez-Pantoja et al., 2008). In the past, a number of groups have attempted to exploit this ability of microbes in the production of cis, cis-muconic acid at the industrial level (Mizuno et al, 1988; Yoshikawa et al, 1990; Choi et al, 1997). In the late 1980s, Celgene Corporation of USA and Mitsubishi Chemical Industries of Japan were active in developing a process for manufacturing muconic acid from toluene and benzoic acid respectively, as evidenced by a number of granted United States and Japanese patents in this area.

A number of microbial organisms have been reported to produce cis, cis-muconic acid using toluene, benzoic acid, benzene or catechol. For example, with catechol as the source of carbon, cis, cis-muconic acid production can be achieved with an almost 100% molar conversion yield using a recombinant E. coli cells expressing the catA gene, which encodes the Pseudomonas putida mt-2 catechol 1,2-dioxygenase responsible for catalyzing ortho-cleavage of catechol, as biocatalyst (Kaneko et al, 2011). Bioreactors for the continuous production of muconic acid using this system have been described.

A recently published international patent application (WO 2011/017560) claims biocatalysts having a muconate pathway and a method for producing muconic acid using these biocatalysts. In brief, this published patent application discloses four different pathways for producing muconic acid. The first pathway for muconic acid production starts with succinyl-CoA and acetyl-CoA. The second pathway for muconic acid production begins with pyruvate and malonate semialdehyde. The third pathway for muconic acid production starts with pyruvate and succinic semialdehyde. The fourth pathway for muconic acid production starts with lysine.

A fermentation route to cis, cis-muconic acid using a genetically engineered E. coli system has been described in the scientific literature (Niu et al., 2002). In 2002, Niu et al published a "benzene free" route to produce adipic acid that used a fermentation process to produce cis, cis-muconic acid, and then a catalytic chemical process to convert the cis, cis-muconic acid to adipic acid. This process has been patented (U.S. Pat. Nos. 5,487,987; 5,616,496). There have been two reports of Saccharomyces cerevisiae yeasts that were genetically engineered to produce cis, cis-muconic acid from glucose (Weber et al., 2012; Curran et al., 2012).

A more recent patent application (WO 2011/085311 A1) describes a bacterial strain producing cis, cis-muconic acid, which is then isomerized into cis, trans-muconic acid.

Recently published International Patent Application No. WO 2013/116244 A1 provides a genetically engineered microorganism that produced cis, cis-muconic acid starting from non-aromatic carbon source, in which all genes coding for protein functioning in a muconic acid pathway are integrated into the chromosomal DNA of said microorganism.

Any one of the microbial strains that have been developed for commercial production of muconic acid using renewable biological feedstock is useful in manufacturing muconic acid useful in the present invention.

As defined in this invention, muconic acid is an unsaturated dicarboxylic acid with six carbon atoms and two double bonds. Based on the geometrical orientation of the terminal carboxylic acid groups, the muconic acid monomers possess cis-cis or trans-trans, trans-cis or cis-trans configuration. The cis-cis, cis-trans, trans-cis and trans-trans isomers are also referred as ZZ, ZE, EZ and EE isomers respectively. Since the two double bonds and two terminal carboxylic acids in the muconic acid act as functional groups, a number of muconic acid derivatives are possible. For example, the reduction of double bonds in the muconic acid yields adipic acid. A condensation reaction between the terminal carboxylic groups in the muconic acid and an alcohol, such as methanol yields dimethyl muconate. Based on this chemical reaction principle, a person skilled in the art will be able to synthesize various muconic acid derivatives including aliphatic esters, aromatic esters, alkyl aromatic esters and aromatic alkyl esters of muconic acid through one or more chemical reaction pathways. For the purpose of clarity, the terms "alkyl aromatic" and "aromatic alkyl" are defined here. Both alkyl aromatic ester of muconic acid and aromatic alkyl ester of muconic acid are derived using muconic acid and an alcohol having both alkyl and aromatic groups and the nature of the bonding with hydroxyl group with aromatic ring determines the name of the alcohol and the resulting muconic acid ester. In the case of alkyl aromatic alcohol, the hydroxyl group is linked to alkyl group and the alkyl group in turn is bonded to an aromatic group. On the other hand, in the case of aromatic alkyl alcohol, the hydroxyl group is directly bonded to the aromatic ring at one carbon and the alkyl group is bonded to another carbon in the aromatic ring.

As defined in this invention, a polymer that contains repeated units of a single monomer is a homopolymer. When identical reactive monomeric units are subjected to polymerization, they react among themselves to form a polymer with certain physical properties. Polystyrene, polyethylene, polypropylene and polyvinyl chloride are some of the well known homopolymers that are widely used in industry. In the present invention, these polymers are referred as conventional polymers as they have been in use for a long period. Despite extensive use of homopolymers resulting from monomers obtained from nonrenewable petrochemical feedstock, production of homopolymers based on the monomers derived from renewable biological feedstock is limited in scope. Polylactide, a biodegradable aliphatic polyester homopolymer derived from lactic acid obtained from renewable resources is an important polymer used in compostable packaging material, upholstery, disposable tableware, microwable tray and other things. Efforts are being made to produce acrylic acid through catalyst-mediated dehydration reaction involving lactic acid and 3-hydroxypropionic acid obtained from renewable biomaterials. Acrylic acid and acrylic acid esters are important commodity chemicals used in the production of polyacrylic esters, elastomers, superabsorbent polymers, floor polishes, adhesives, paints, and the like. Similarly, succinic acid derived from biological feedstock such as glucose, sucrose and glycerol is used in the production of polybutyl succinate (PBS), a growing biodegradable alternative to some commonly used plastics.

As defined in the present invention, the term "muconic monomer" includes muconic acid monomers and its derivatives. The muconic acid monomers can exist in one of the four isomeric forms namely EZ isomer, ZZ isomer, EE isomer and ZE isomer. The list of muconic acid derivatives suitable for the manufacture of one or other types of polymers according to the present invention includes alkyl, aryl, alkyl aromatic and aromatic alkyl esters of muconic acid. Monomers of muconic acid derivatives also exist in four different isomeric forms namely EZ isomer, ZZ isomer, EE isomer and ZE isomer as illustrated in the FIGS. 1, 3, 5, 7 and 9. The monomeric muconic acid derivatives assume the isomeric form of the muconic acid monomer from which they are derived. Muconic isomers useful in the present invention are derived either from renewable feedstock such as glucose, sucrose, cellulosic hydrolysate and glycerol or from nonrenewable feedstock such as phenol, benzoic acid and catechol. In the present invention, muconic acid monomers and monomers of muconic acid esters are polymerized with the aid of an internal or external catalyst to produce muconic acid homopolymers and muconic polyester homopolymers respectively (FIG. 1). Depending upon the original isomeric form of the starting muconic monomer four different isomeric forms of homopolymers namely Racemo Disyndiotactic polymer, Racemo diisotactic polymer, Meso diisotactic polymer, and Meso disyndiotactic polymer are produced as illustrated in FIG. 1.

When two or more different polymers are mixed together, the resulting polymer is called copolymer and the process is referred as copolymerization. Copolymers that are obtained by mixing two different polymers, three different polymers and four different polymers are referred as bipolymer, tripolymer and tetrapolymers respectively. Commercially relevant copolymers include acrylonitrile-butadiene-styrene (ABS) plastic, styrene-butadiene rubber (SBR), nitrile rubber, styrene-acrylonitrile, styrene-isoprene-styrene (SIS) and ethylene-vinyl acetate. Copolymerization is used to modify the properties of manufactured plastics to meet specific needs, for example to reduce crystallinity, modify glass transition temperature or to improve solubility. Copolymers are also used as a way of improving mechanical properties, in a technique known as rubber toughening. ABS (acrylonitrile butadiene styrene) is a copolymeric system where elastomeric phases within a rigid matrix act as crack arrestors and increase the energy absorption when the material is impacted. Various muconic polymers can be combined with other conventional polymers to produce polymers with certain desirable physical and chemical properties.

In another embodiment of the present invention a process for producing cross-linked muconic polymers is provided. When the term "cross-linking" is used in polymerization reaction, it usually refers to the use of cross-links to promote a difference in the physical properties of the resulting polymer. As defined in the present invention, cross-link is a connection that links one polymer chain to another polymer chain through the use of a monomer. Cross-links can be a chemical cross-link, physical cross-link or an oxidative cross-link depending on the nature of the formation of the cross-link and the process used to form them. In a chemical cross-link, cross-links are formed by chemical reactions that are initiated by heat, pressure and change in pH or irradiation. Cross-link can be covalent bonds or ionic bonds. Chemical cross-links are irreversible and are thermally and mechanically stable. Once formed chemical cross-links are difficult to break. In some cases, if the chemical cross-links are sufficiently different from the bonds forming the polymers, the cross-linking process can be reversed. On the other hand physical cross-links are not covalently bound to the polymers but rather rely on the layer interlocking ability in their microstructure to achieve stability. Physical cross-links offer a much wider range of properties than chemical cross-links because the domains that act as cross-links are reversible and can be reformed by heat. Some polymers can undergo oxidative cross-linking when exposed to atmospheric oxygen. When the formation of cross-links by oxidation is desirable, an oxidizer such as hydrogen peroxide may be used to speed-up the process.

In preferred aspect of this embodiment, a monomer other than the monomers present in polymeric chains being cross-linked is used as a cross-link. In one aspect of this embodiment, in the first step of the reaction, muconic acid homopolymers and muconic polyester or muconic polyamide homopolymers are produced as described in the embodiment above. In the second step of the reaction, polymeric chains of muconic acid homopolymer and muconic polyester homopolymer are cross-linked using monomers selected from a group consisting of ethylene, propylene, acrylic acid, methaacrylic acid, acrylonitrile, styrene, butadiene and isoprene monomers. Monomers used in cross-linking the muconic polymers can either be a single monomer or a mixture of monomers.

Figure 3:
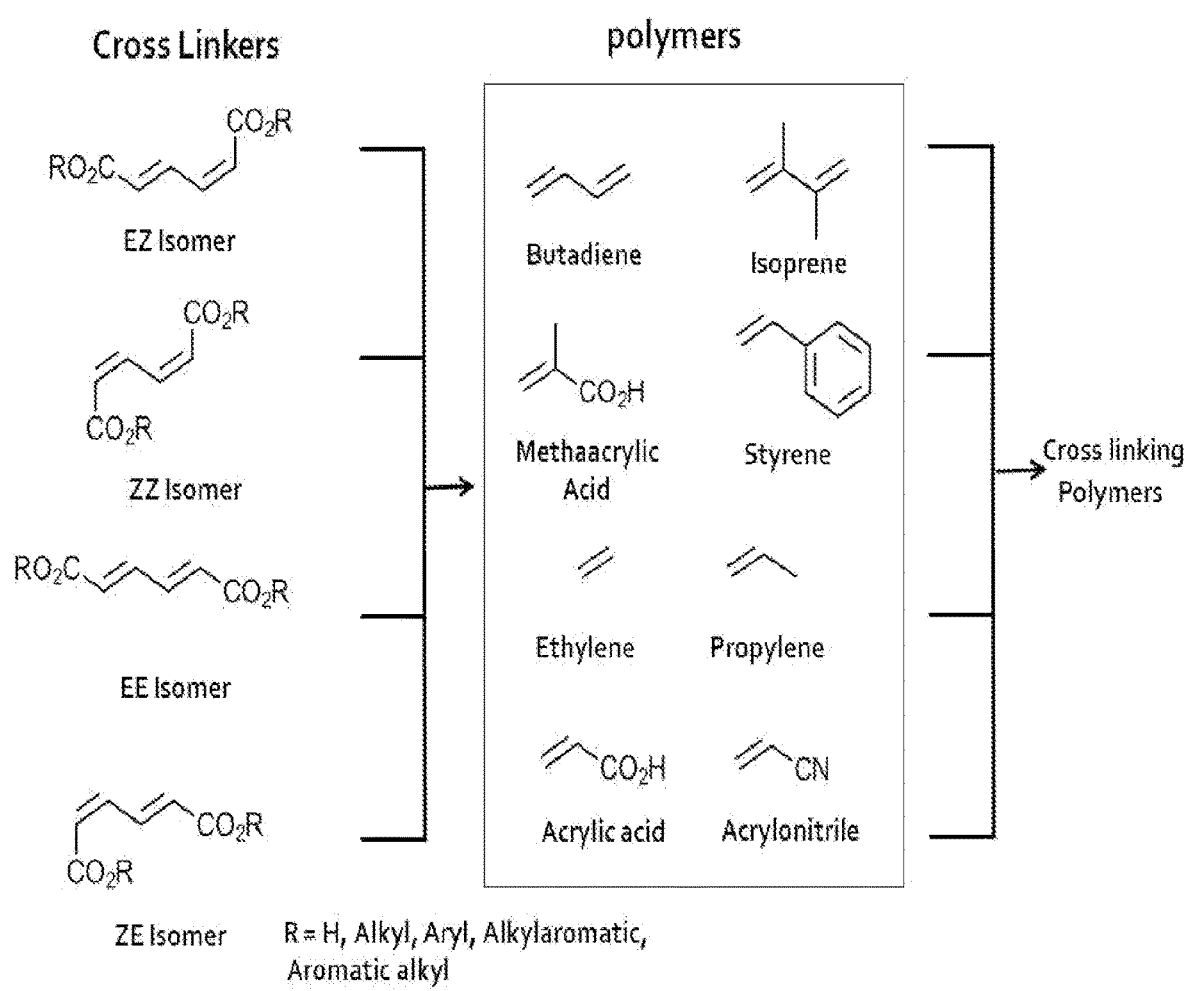
FIG. 3. Use of muconic monomers as crosslinkers in the conventional polymer preparations. The muconioc acid monomer and its derivatives including aliphatic esters, aromatic esters, alkyl aromatic esters and aromatic alkyl esters of muconic acid are useful as crosslinkers in the conventional polymer preparations. Either a single isomeric form of muconic monomer or a mixture of isomers of muconic monomers including EZ isomer, ZE isomer, EE isomer and ZZ isomer can be used as cross-linkers in the conventional polymer preparation. One or more types of muconic monomers are directly introduced into the polymerization process for the production polybutadiene, polyisoprene, polyacrylic acid, polyacrlyonitrile, polyethylene, polypropylene, polystyrene, and polymethaacrylic acid. Besides muconic monomers, other monomers selected from a group consisting of butadiene, isoprene, methaacrylic acid, styrene, ethylene, propylene, acrylic acid, and acrylonitrile can also be used as a crosslinkers in the polymer preparation. The muconic acid and its derivatives as well as other monomers used in this polymerization reaction are derived either from renewable biomass resources through fermentation or from nonrenewable petrochemical feedstock through chemical catalytic processes or biological conversion.

In another aspect of this embodiment, one or other muconic isomers are used as cross-links in polymerization process. Muconic monomers either in its isomerically pure form such as EZ isomer, ZE isomer, EE isomer and ZZ isomers or a mixture of some or all of the isomers can be directly introduced to the polymerization process leading to the manufacture of cross-linked polybutadiene, polyisoprene, polyacrylic acid, polyacrlyonitrile, polyethylene, polypropylene, polystyrene, polymethaacrylic acid as illustrated in FIG. 3. Muconic monomers suitable for use as a cross-link in the manufacture of cross-linked polymers include muconic acid monomers and its derivatives including aliphatic esters, aromatic esters, alkyl aromatic esters and aromatic alkyl esters of muconic acid.

Figure 4:
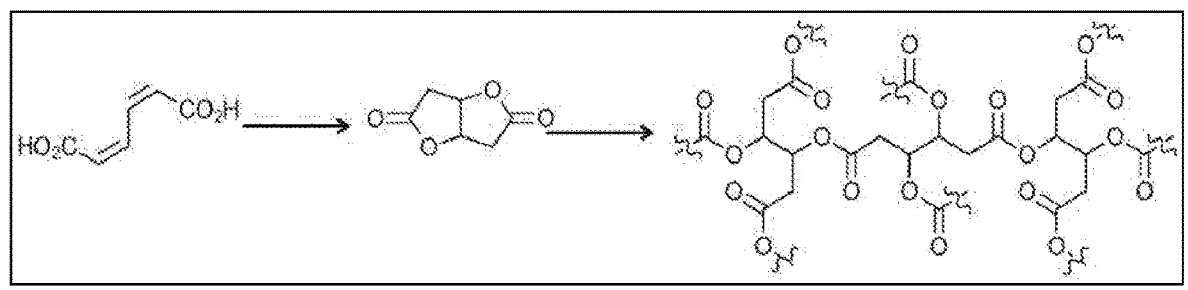
FIG. 4. Ring opening polymerization of mucono bis-lactone. The ring opening polymerization of mucono bis-lactone is initiated with ZZ isomer of muconic acid using anionic initiator such as BrØnsted base or cationic initiators such as Lewis acid. The ZZ isomer of muconic acid used in this ring opening polymerization reaction is derived either from renewable biomass resources through fermentation or from nonrenewable petrochemical feedstock through chemical catalytic processes or biological conversion FIG. 5. Condensation polymerization reaction to produce muconic polyesters. In this condensation polymerization process, muconic acid or its derivatives are subjected to an esterification reaction with a diol leading to the production of a muconic polyester. Esterification reaction can be a self-catalyzed reaction or assisted by an external catalyst. Polymer chain length may vary depending on the reaction condition and the catalyst used for the reaction. The muconic acid and its derivatives as well as the diol used in this polymerization reaction are derived either from renewable biomass resources through fermentation or from nonrenewable petrochemical feedstock through chemical catalytic processes or biological conversion. Muconic acid derivatives used in this polymerization process can be aliphatic esters, aromatic esters, alkyl aromatic esters and aromatic alkyl esters of muconic acid. Muconic isomers useful in this condensation polymerization reaction can be isomerically pure EZ isomer, ZE isomer, EE isomer, ZZ isomers or a mixture of some or all of these isomers. Diols used in this example can be a saturated or unsaturated aliphatic diols, aromatic diols or heteroaromatic diols and the number of carbon atoms in between the two terminal carbon atoms ranges from 0 to 10.

Ring-opening polymerization (ROP) is a form of chain-growth polymerization, in which the terminal end of a polymer chain act as a reactive center where further cyclic monomers can react by opening its ring system and form a longer polymer chain. The propagating center can be a radical, an anionic species or a cationic species. Some cyclic monomers such as norbornene or cyclooctadiene can be polymerized to high molecular weight polymers by using metal catalyst. Anionic ring-opening polymerizations (AROP) are ring-opening polymerizations that involve nucleophilic reagents as initiators. Monomers with a ring structure are able to undergo anionic ROP due to the ring-distortion. Ring-opening will be triggered by the nucleophilic attack of the initiator to the carbon, forming a new species that will act as a nucleophile. The sequence will repeat until the polymer is formed. Some of the well known ring-opening polymer products are Nylon-6, and Polylactic acid. Monomers with strained cycles can be synthesized from muconic acid isomers through a single step or multi step process. These strained cyclic esters can be attractive monomers for ring-opening polymerization. The resulting polyesters can have properties that are of broad application interest. The properties of these products may provide biodegradable and renewable alternative to traditional plastics. In another embodiment, cis-cis muconic acid isomer is converted to mucono bis-lactone through a process called lactonization. Mucono Bis-lactone can be directly used in polymeric applications such as ring opening polymerization as illustrated in FIG. 4.

Condensation polymers are formed through a condensation reaction, where two molecules join together with the removal of small molecule such as water or methanol as a byproduct. Types of condensation polymers include polyamides, polyacetals and polyesters. Condensation synthesis often involves joining monomers with hydroxyl group (—OH) or amines (—NH2) and monomers with carboxylic acid group (—COOH). Typically, two or more monomers are used in a reaction. Polyesters are created through a reaction between a carboxylic acid group (—COOH) and a hydroxyl group (—OH). Polyamides are created through a reaction between a carboxylic acid group (—COOH) and an amine (—NH2). Condensation polymers are called linear condensation polymer when it contains a long string of carbon-carbon bonds or branched condensation polymer when it branches at irregular intervals along the polymer chain. Many condensation polymers including polyesters, polyamides and polycarbonates are widely used to make plastic products such as films, bottles, and other molded products. The mechanical and physical properties of these polymers are highly dependent on their molecular weights. The typical process to produce polyester or polyamide involves reacting petrochemical derived diacids with diols or diamines. The interest in developing condensation polymers using monomers derived from renewable biological feedstock have been growing. Polybutyl Succinate (PBS) is a condensation product of succinic acid and butanediol and it is considered as a biodegradeable alternative to some common plastics. Similarly, muconic acid can also be condensed with diols and diamines to yield polyester and polyamides respectively. This polymer products resulting from the condensation reaction between renewable muconic acid and renewable diols or diamines may act as a replacement for traditional plastic products derived from nonrenewable petrochemical feedstock.

Figure 5:
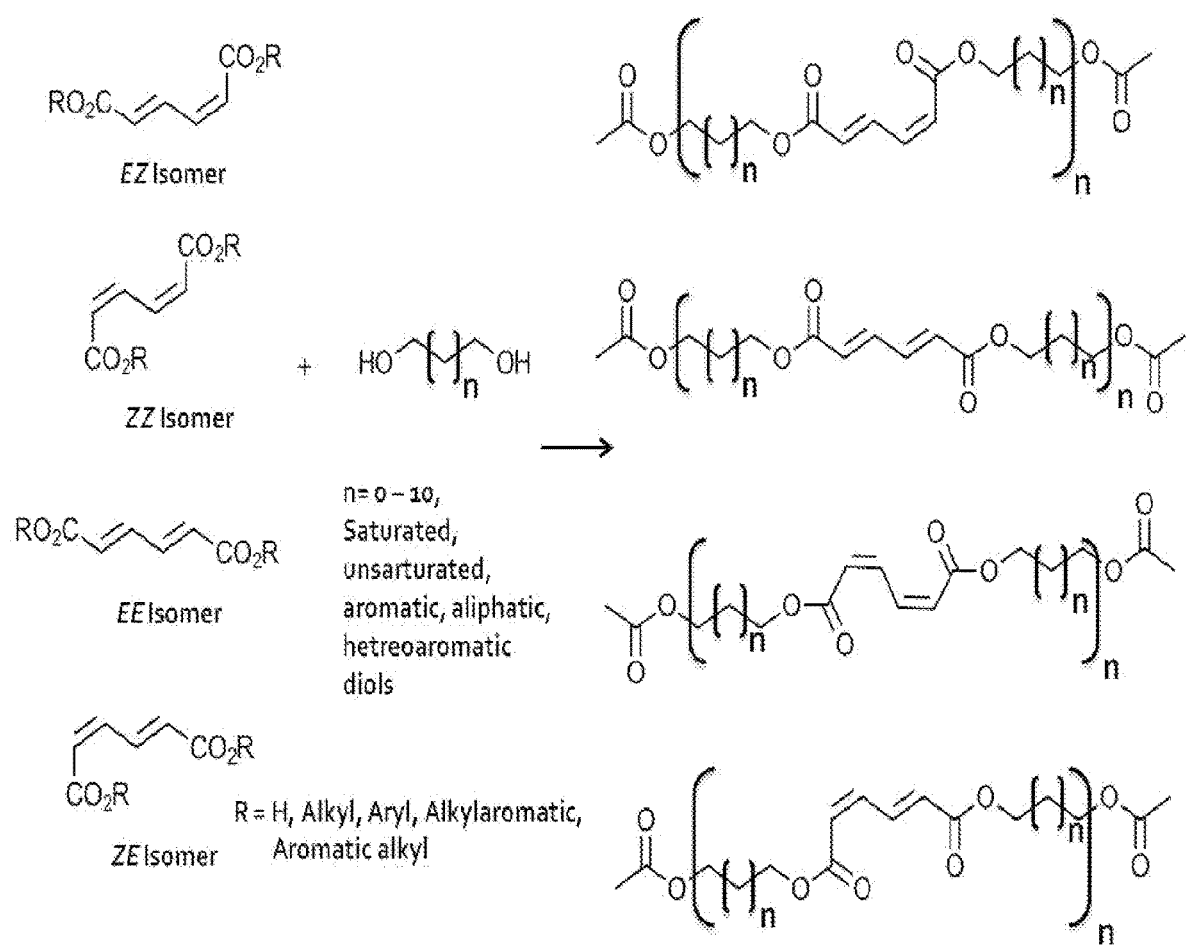
Figure 6:
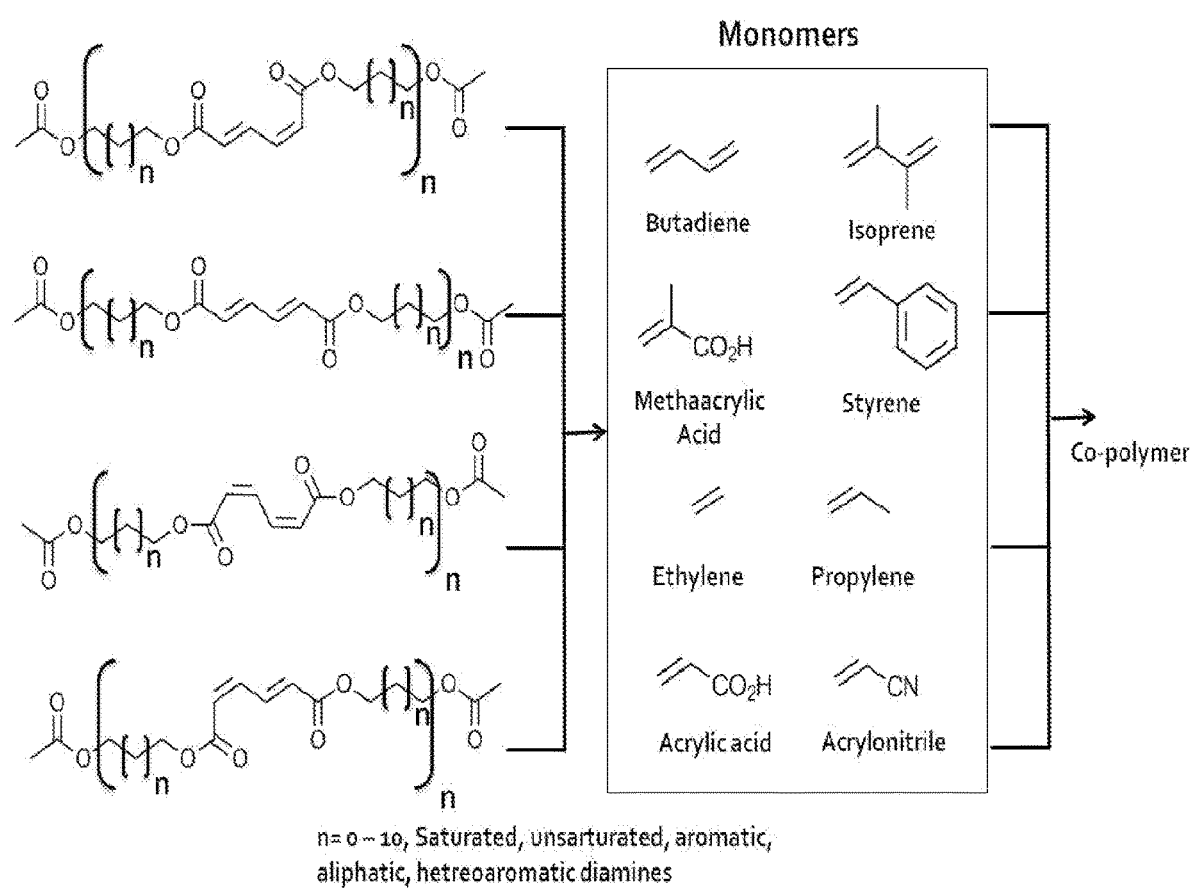
FIG. 6. Preparation of copolymers comprising one or more muconic polyesters and conventional polymers based on monomers selected from a group consisting of butadiene, isoprene, acrylic acid, methaacrylic acid, styrene, acrylonitrile, ethylene and propylene. The individual polymers are prepared separately and are physically mixed together to yield a copolymer. In the first step of this polymerization process, muconic isomer is subjected to an esterification reaction with diols leading to the production condensation polyester products. In the second step, the polyester from the first step is physically mixed with one or more conventional polymers derived from monomers such as ethylene, propylene, acrylic acid, methaacrylic acid, acrylonitrile, styrene, butadiene, isoprene to the produce co-polymer products. Muconic isomers used in this process can be muconic acid and its derivatives including aliphatic esters, aromatic esters, alkyl aromatic esters and aromatic alkyl esters of muconic acid. Muconic isomers useful in this condensation polymerization reaction can be isomerically pure EZ isomer, ZE isomer, EE isomer and ZZ isomers or a mixture of some or all of these isomers. Diols used in this copolymerization reaction can be a saturated or unsaturated aliphatic diols, aromatic diols or heteroaromatic diols and the number of carbon atoms in between the two terminal carbon atoms ranges from 0 to 10. The muconic and diol monomers used in the preparation of muconic polyesters as well as the monomers useful in the preparation of conventional polymers are derived either from renewable biomass resources through fermentation or from non-renewable petrochemical feedstock through chemical catalytic processes or biological conversion.

In one embodiment of the present invention, muconic monomers either in its isomerically pure form such as EZ isomer, ZE isomer, EE isomer and ZZ isomers or a mixture of some or all of the isomers is subjected to an esterification reaction with diols leading to the production of muconic polyester polymer. Muconic polyesters produced in this process can be in an isomerically pure form or mixture of one or more different isomers depending on the polymerization condition and the catalyst used in the polymerization process. Muconic monomers used in this embodiment can be muconic acid or aliphatic esters, aromatic esters, alkyl aromatic esters and aromatic alkyl esters of muconic acid. Diols used in this example can be a saturated or unsaturated aliphatic diols, aromatic diols or hetreoaromatic diols where the number of carbon atoms in between the two terminal carbon atoms is in the range of 0 to 10 as illustrated in FIG. 5.

In an another aspect of this embodiment, the polymer chains in a muconic acid polyester are cross-linked using one or other monomers selected from a group consisting of ethylene, propylene, acrylic acid, methaacrylic acid, acrylonitrile, styrene, butadiene, and isoprene to produce a cross-linked polymer. Monomers used in the manufacture of cross-linked muconic polyester polymer can be a single monomer or a mixture of monomers. The cross-linking reaction according to this embodiment can be catalyzed by an internal or external catalyst. Physical and chemical properties of the resulting cross-linked muconic polyester polymers may vary depending on the reaction condition and the catalyst used in the cross-linking process.

Figure 7:
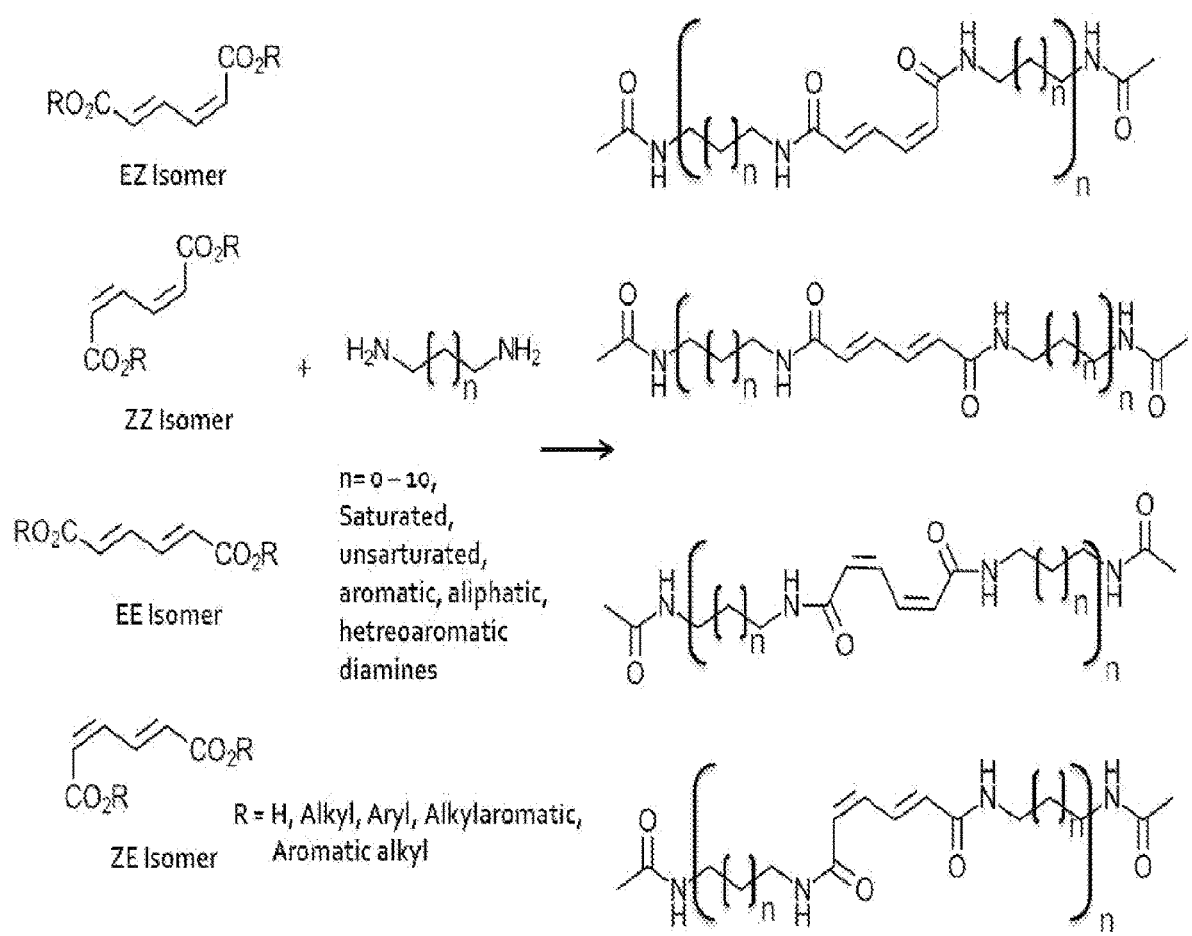
FIG. 7. Condensation polymerization reaction to produce muconic polyamides. In this condensation polymerization process, muconic acid and its derivatives are subjected to an amination reaction with a diamine leading to the production of muconic polyamide. Amination reaction can be a self-catalyzed reaction or assisted by an external catalyst. Polymer chain length may vary depending on the reaction condition and the catalyst used for the reaction. The muconic acid and its derivatives as well as the diamines used in this co-polymerization reaction are derived either from renewable biomass resources through fermentation or from non-renewable petrochemical feedstock through chemical catalytic processes or biological conversion. Muconic isomers used in this process can be muconic acid and its derivatives including aliphatic esters, aromatic esters, alkyl aromatic esters and aromatic alkyl esters of muconic acid. Muconic acid isomers useful in this condensation polymerization reaction can be isomerically pure EZ isomer, ZE isomer, EE isomer and ZZ isomers or a mixture of some or all of these isomers. Diamines used in this example can be saturated or unsaturated aliphatic diamines, aromatic diamines or heteroaromatic diamines and the number of carbon atoms in between the two terminal carbon atoms ranges from 0 to 10.
Figure 8:
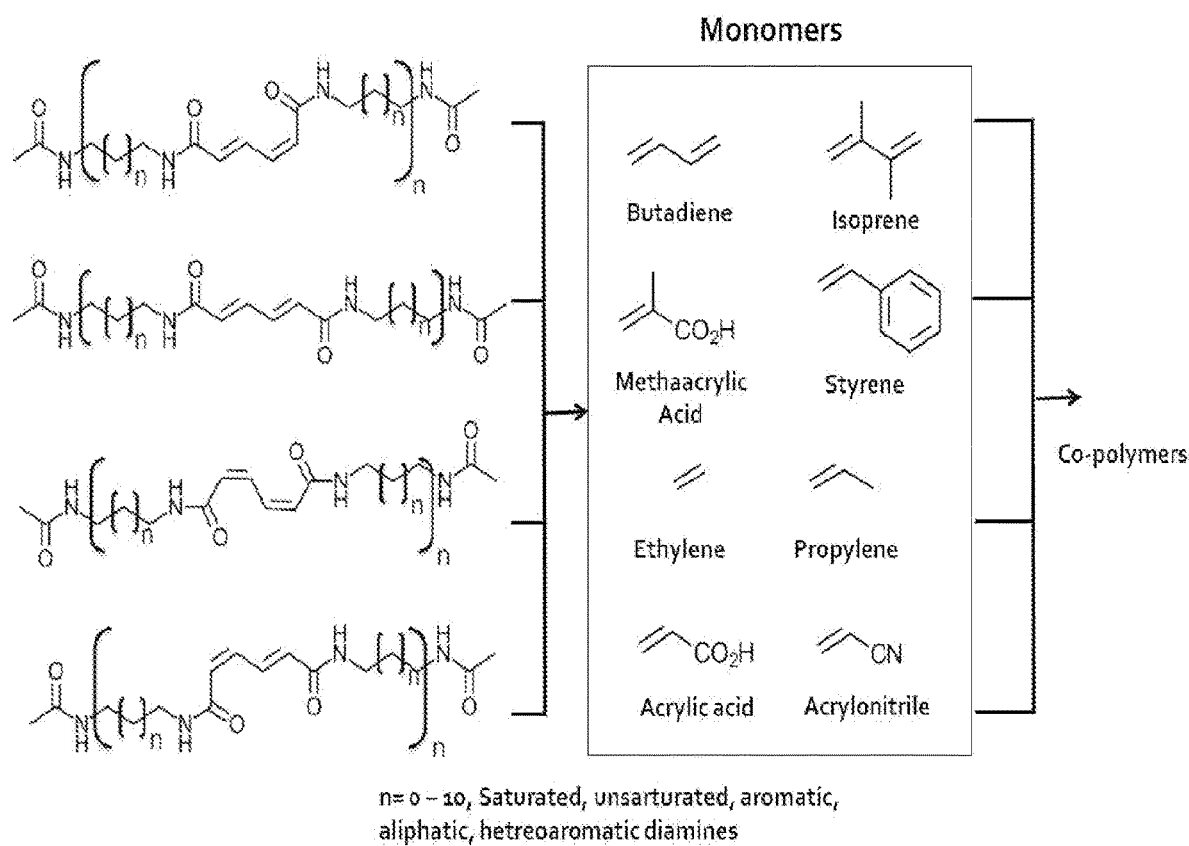
FIG. 8. Preparation of copolymers comprising one or more muconic polyamides and conventional polymers based on monomers selected from a group consisting of butadiene, isoprene, acrylic acid, methaacrylic acid, styrene, acrylonitrile, ethylene and propylene. The individual polymers are prepared separately and are physically mixed together to yield a copolymer. In the first step of this polymerization process, muconic isomer is subjected to an amination reaction with diamines leading to the production condensation polyester products. In the second step, the polyester from the first step is physically mixed with one or more conventional polymers derived from monomers such as ethylene, propylene, acrylic acid, methaacrylic acid, acrylonitrile, styrene, butadiene, isoprene to the produce co-polymer products. Muconic isomers used in this process can be muconic acid and its derivatives including aliphatic esters, aromatic esters, alkyl aromatic esters and aromatic alkyl esters of muconic acid. Muconic isomers useful in this condensation polymerization reaction can be isomerically pure EZ isomer, ZE isomer, EE isomer and ZZ isomers or a mixture of some or all of these isomers. Diamines used in this copolymerization reaction can be a saturated or unsaturated aliphatic diamines, aromatic diamines or heteroaromatic diamines and the number of carbon atoms in between the two terminal carbon atoms ranges from 0 to 10. The muconic and diamine monomers used in the preparation of muconic polyesters as well as the monomers useful in the preparation of conventional polymers are derived either from renewable biomass resources through fermentation or from non-renewable petrochemical feedstock through chemical catalytic processes or biological conversion FIG. 9. Production of 2, 5 dimethylene-3-enedioic acid and its derivatives from muconic acid and its derivatives. In the first step of this reaction pathway, muconic acid and its derivatives including aliphatic esters, aromatic esters, alkyl aromatic esters and aromatic alkyl esters of muconic acid are subjected to an electrochemical reaction leading to the production of hex-3-enedioic acid. Electrochemical reaction used in this process can be a simple electrolysis or an electrochemical reaction promoted by mixing two or more chemicals. In the second step of this reaction pathway, hex-3-enedioic acid resulting from the first step of the reaction is subjected to a condensation reaction with an aldehyde or a ketone. This condensation reaction can involve an acid, a base, a Lewis acid or a BrØnsted base. The muconic acid and its derivatives useful as a starting material for the production of 2, 5 dimethylene-3-enedioic acid is derived from renewable biomass resources through fermentation or from nonrenewable petrochemical feedstock through chemical catalytic processes or biological conversion. Hex-3-enedioic acid could be used in a variety of polymeric applications including but not limited to condensation polymerization, copolymerization and homopolymerization. 2, 5 dimethylene-3-enedioic acid is useful in a variety of applications including, but not limited to, adhesives. In addition, 2, 5 dimethylene-3-enedioic acid can also be used in condensation polymerization, copolymerization and homopolymerization reactions.
Figure 9:
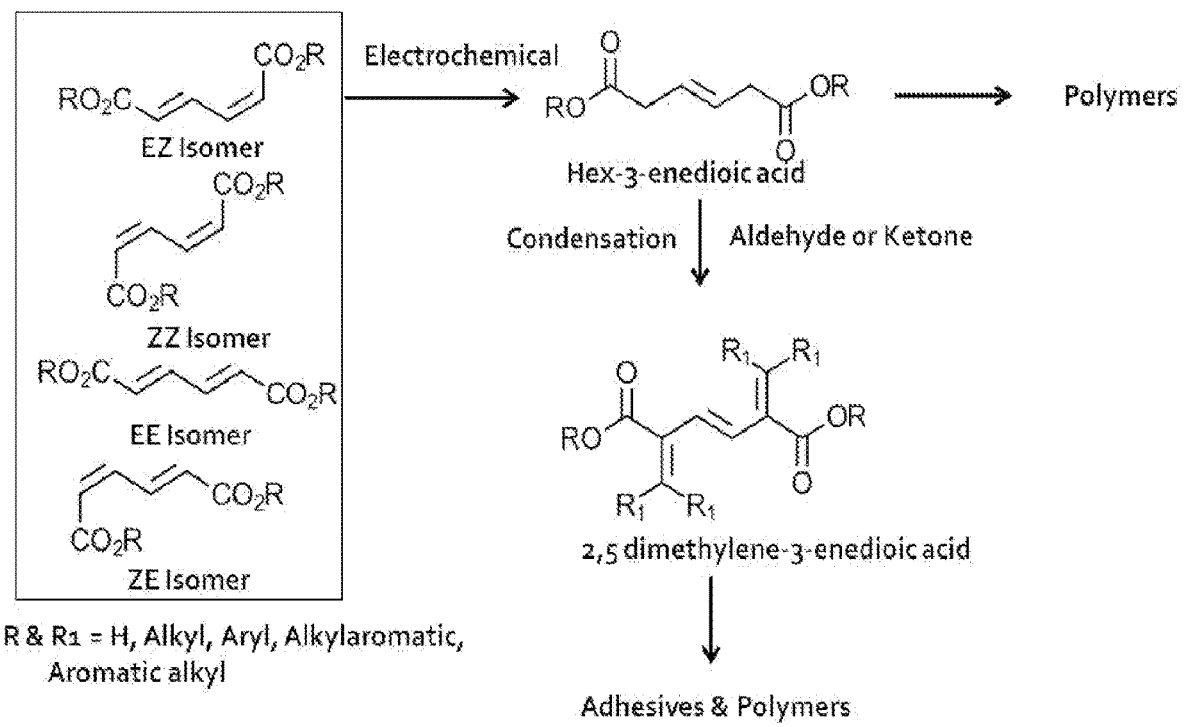
Figure 10:
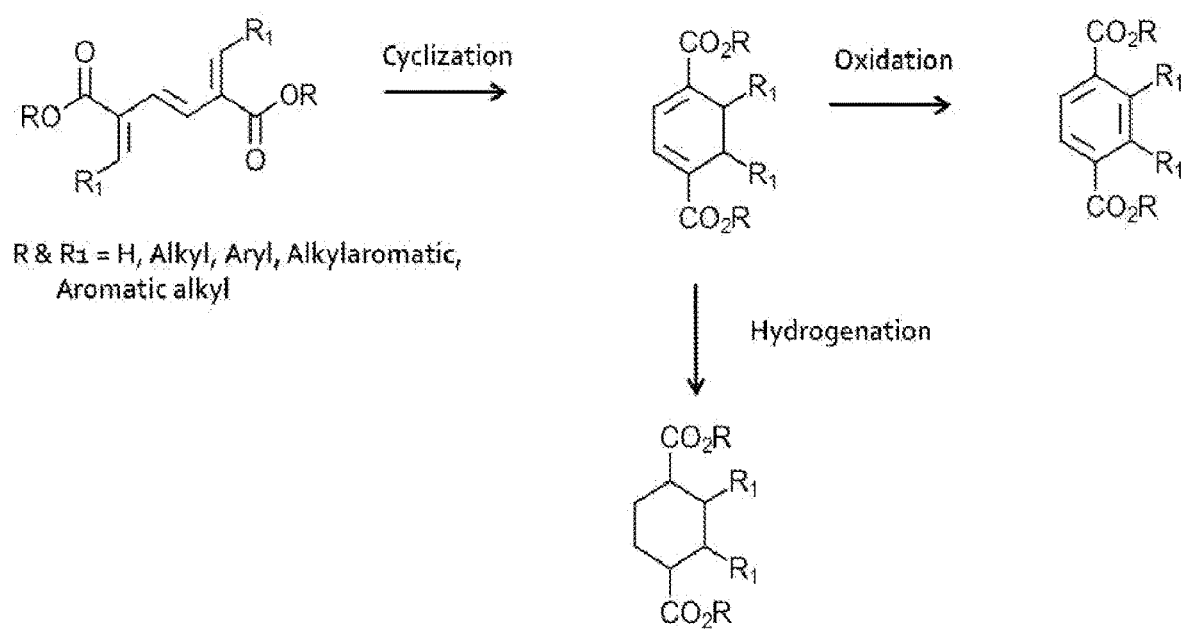
FIG. 10. A process for preparing terephthalic acid and its derivatives from 2, 5 dimethylene-3-enedioic acid and its derivatives. The 2, 5 dimethylene-3-enedioic acid and its derivatives obtained from muconic acid and its derivatives including aliphatic esters, aromatic esters, alkyl aromatic esters and aromatic alkyl esters of muconic acid as described in the FIG. 9 are subjected to a cyclization reaction to obtain dihydroterephthalic acid as an intermediate product. In the second step of this reaction pathway, dihydroterephthalic acid is hydrogenated to cyclohexane dicarboxylic acid. In another reaction pathway, dihydroterephthalic acid is oxidized to form terephthalic acid. 2, 5 dimethylene-3-enedioic acid derivatives used in this reaction process can be aliphatic esters, aromatic esters, alkyl aromatic esters and aromatic alkyl esters of 2, 5 dimethylene-3-enedioic acid.
Figure 11:
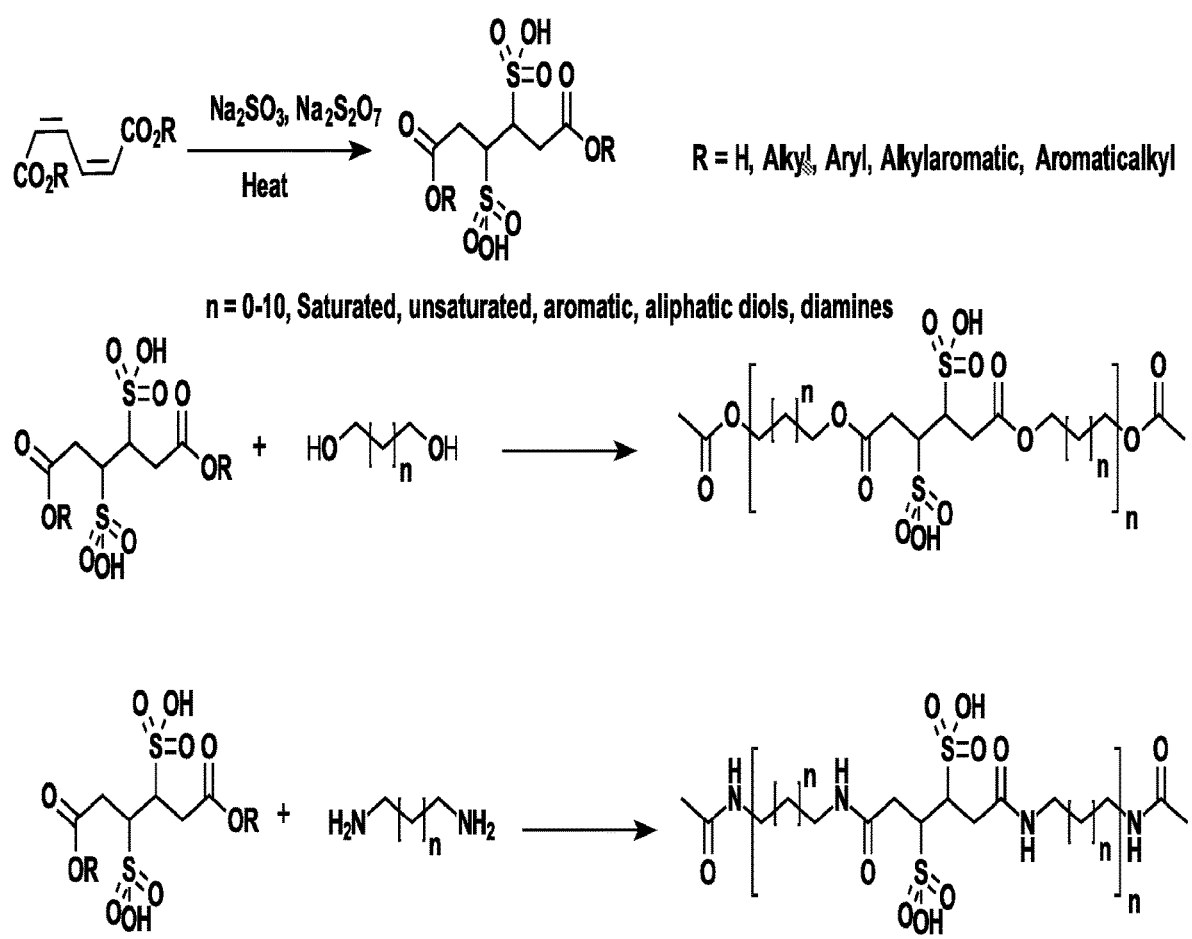
FIG. 11. A process for preparing 3,4-disulfohexanedioic acid and its derivatives from muconic acid and its derivatives. The muconic acid and its derivatives including aliphatic esters, aromatic esters, alkyl aromatic esters and aromatic alkyl esters are subjected to a sulfonation reaction with sodium sulfite and sodium metabisulfite mixture under alkaline reaction conditions. The resulting mixture is acidified and purified to produce pure 3,4-disulfohexanedioic acid crystals. In another reaction pathway, muconic acid is also treated with sulfurdioxide in alkaline reaction conditions to produce 3,4-disulfohexanedioic acid. Polymerization reaction of 3,4-disulfohexanedioic acid is performed with diols and diamines under solvent free conditions in the presence of metal catalyst to facilitate dehydration process. After the complete removal of water under vacuum, the polymer is poured into an aluminum foil and molded into desired shapes.
Figure 12:
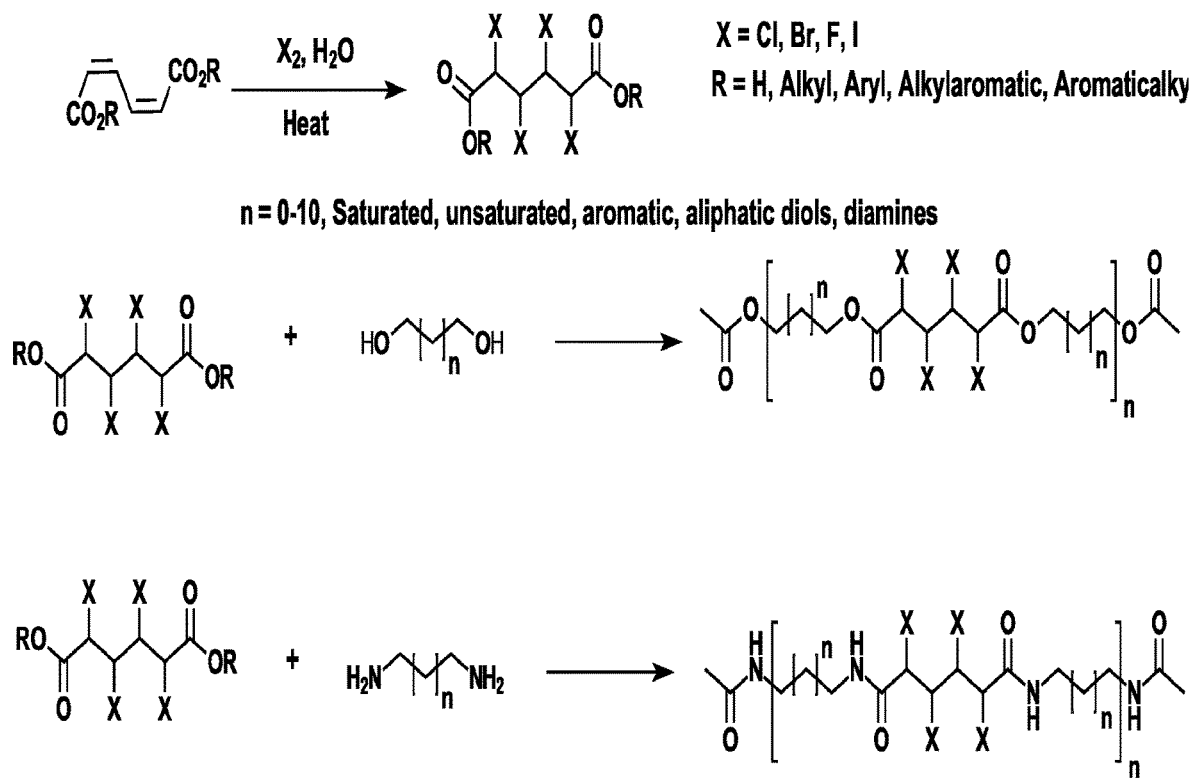
FIG. 12. A process for preparing 2,3,4,5-tetrahalohexanedioic acid and its derivatives from muconic acid and its derivatives. The muconic acid and its derivatives including aliphatic esters, aromatic esters, alkyl aromatic esters and aromatic alkyl esters are subjected to a halogenation reaction with a halogen (bromine, chlorine, fluorine and iodine) and water mixture under neutral reaction conditions. The product is precipitated and isolated as a crystalline solid. In another reaction pathway, 2,3,4,5-tetrahalohexanedioic acid is also produced by using halogenations reagents such as N-halosuccinamide, hypohalous acid and sodium hypohalides. Polymerization reaction of 2,3,4,5-tetrahalohexanedioic acid is performed with diols and diamines under solvent free conditions in the presence of metal catalyst to facilitate dehydration process. After the complete removal of water under vacuum, the polymer is poured into an aluminum foil and molded into desired shapes.

In yet another embodiment of the present invention, muconic monomers either in its isomerically pure form such as EZ isomer, ZE isomer, EE isomer and ZZ isomer or a mixture of some or all of the isomers is subjected to a condensation polymerization reaction with diamines leading to the production of muconic polyamides. Polyamides produced in this process can be in an isomerically pure form or mixture of one or more different isomers depending on the muconic monomers used, polymerization condition and the catalyst used in the polymerization process. Muconic monomers used in this embodiment can be one or other isomers of muconic acid or aliphatic esters, aromatic esters, alkyl aromatic esters and aromatic alkyl esters of muconic acid. Diamines used in this example can be a saturated or unsaturated aliphatic diamines, aromatic diamines or hetreoaromatic diamines where the number of carbon atoms in between the two terminal carbon atoms may range from 0 to 10 as illustrated in FIG. 7.

In an another aspect of this embodiment, the polymer chains in a muconic polyamides are cross-linked using one or other monomers selected from a group consisting of ethylene, propylene, acrylic acid, methaacrylic acid, acrylonitrile, styrene, butadiene and isoprene to produce a cross-linked polymer. Monomers used in the manufacture of cross-linked muconic polyamide polymer can be a single monomer or a mixture of monomers. The cross-linking reaction according to this embodiment can be catalyzed by an internal or external catalyst. Physical and chemical properties of the resulting cross-linked muconic polyamide polymers may vary depending on the reaction condition and the catalyst used in the cross-linking process.

In another embodiment of the present invention, muconic monomers including muconic acid and its derivatives including aliphatic esters, aromatic esters, alkyl aromatic esters and aromatic alkyl esters of muconic acid are subjected to an electrochemical reaction leading to the production of hex-3-enedioic acid. Electrochemical reaction used in this process can be a simple electrolysis or an electrochemical reaction promoted by mixing two or more chemicals. As is the case with other embodiments of the present invention, the muconic monomers useful as a starting material for the production of hex-3-enedioic acid is derived from renewable biomass resources through fermentation or from nonrenewable petrochemical feedstock through chemical catalytic processes or biological conversion. Hex-3-enedioic acid resulting from the electrochemical reaction is reacted with an aldehyde or a ketone to yield 2, 5 dimethylene-3-enedioic acid which can be used in adhesive applications. In another aspect of this embodiment, hex-3-enedioic acid is subjected to polymerization reaction including but not limited to condensation polymerization, copolymerization and homopolymerization to produce polyester, polyamides, homopolymers and cross-linked polymers. In another aspect of this embodiment, hex-3-enedioic acid is converted to 2, 5 dimethylene-3-enedioic acid. 2, 5 dimethylene-3-enedioic acid is used in applications related to adhesives. 2, 5 dimethylene-3-enedioic acid is also useful as a starting material in the preparation of homopolymer, polyester homopolymer, polyamides homopolymers, cross-linked polymers and co-polymers. In yet another aspect of this embodiment, 2, 5 dimethylene-3-enedioic acid is cyclized to yield dihydroterephthalic acid. Dihydroterephthalic acid is converted to terephthalic acid through an oxidation reaction. Alternately, dihydroterephthalic acid is hydrogenated to produce cyclohexane diacid (CHDA). Terephthalic acid is useful in the production of polyethylene terephthalate (PET) used in plastic container bottles. Cyclohexane diacid (CHDA) is hydrogenated to produce cyclohexane dimethanol (CHDM). CHDM is widely used in polycarbonate related polymeric applications. CHDA is used in polyester and polyamides related applications. When starting with 2, 5 dimethylene-3-enedioic ester, it is possible to obtain dihydroterephthalic acid ester which upon further hydrogenation yields cyclohexane dicarboxylic acid ester. Dihydroterephthalic acid ester upon further oxidation yields terephthalic acid ester.

In another embodiment of the present invention, muconic monomers including muconic acid and its derivatives including aliphatic esters, aromatic esters, alkyl aromatic esters and aromatic alkyl esters of muconic acid are subjected to a sulfonation reaction leading to the production of 3,4-disulfohexanedioic acid. Sulfonation of muconic acid and its derivatives is achieved using sulfonating agents such as sodium sulfite or sodium thiosulfate well known in the art. Sulfur dioxide is also used as means and methods for the sulfonation of muconic acid. Carboxylic acids are selectively functionalized in the presence of sulfonic acid. Simple carboxylic esters and amides with free sulfonic acid group are used as surfactants in many surface related applications. Carboxylic esters and amides with sulfonic acid salts are also made and used as components in soaps and detergents. Polyesters and polyamides with free sulfonic acid group or sulfonic acid metal salt group are made by selective polymerization of carboxylic acid in 3,4-disulfohexanedioic acid. The polymers are used as ion exchange resins or proton exchange resins in several industrial applications. Acidic and basic properties of the polymers are easily modified by choosing appropriate buffers to neutralize the properties of the polymers.

In another embodiment of the present invention, muconic monomers including muconic acid and its derivatives including aliphatic esters, aromatic esters, alkyl aromatic esters and aromatic alkyl esters of muconic acid are subjected to a halogenation reaction leading to the production of 2,3,4,5-tetrahalohexanedioic acid. Halogenation procedures used in this invention involves the use of simple halogenating agents such as fluorine, chlorine, bromine and iodine. More active halogenating reagents such as N-halosuccinamide hypohalous acid and metal hypohalides are also useful as means and methods for the halogenation of muconic acid. Carboxylic acids are easily functionalized in the presence of halogens to form diesters or diamides. 2,3,4,5-tetrabromohexanedioic esters are used in fire prevention coatings, fire withstanding coatings and surface modification applications. 2,3,4,5-tetrabromohexanedioic amides are used as coalescing material to improve fire and heat withstanding properties of the polymers. Polyesters and polyamides with free halogen group are made by polymerization of 2,3,4,5-tetrabromohexanedioic acid and are used to make fire and heat resistant fibers and materials. These polymeric materials are used on the surface of other fire sensitive materials. These polymers are also used to produce water repellent materials and fibers useful in the under-water electrical applications.

Example 1

Synthesis of Petro-Muconic acid

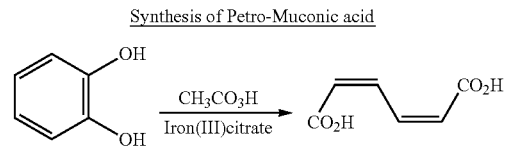

Peracetic acid was prepared from acetic anhydride as described here. 5 L of acetic anhydride was added to the 3 L of 35% H2O2 flask dropwise and the temperature was controlled below 40° C. over 7 hours. The reaction mixture was stirred overnight at room temperature to ensure complete conversion to peracetic acid. The resulting solution was used as such for the subsequent synthesis. 12 g of Iron (III) citrate was added to the reaction mixture. It was stirred for 4 hours till the formation of red homogeneous mixture was complete. 700 g of catechol was dissolved in 1.5 L of acetic acid and was added to the reaction mixture dropwise over 7 hour period. The reaction mixture was kept between 30° C. to 38° C. The reaction mixture was stirred for another 2 hours. The reaction color became dark brown gradually. The reaction mixture was cooled to 10° C. under ice bath and it was filtered cold, washed with acetic acid and acetone and dried under vacuum oven for 5 h at 50° C. to yield 180 g of muconic acid as a pale yellow powder.

Example 2

Synthesis of Bio-Muconic Acid

An *Escherichia coli* strain genetically modified to produce muconic acid was grown in a small scale (200 microaerobic fermentor at 37° C. using a defined medium containing 100 g/L glucose supplemented with 10 microgram/l: biotin, 1 niacin, and 1 mg/L thiamine hydrochloride. The culture flask was shaken on a rotary shaker at 270 RPM. pH was set at 7.0 and controlled by addition of 2 M NH4OH as needed. 15 muconic acid was produced in 192 hours. The fermentation broth was centrifuged to remove cell mass. A pre-filtration with 300 micron filter paper was used to remove the residual solid after centrifuge. A 10 KD ultra filtration was performed to remove macro molecules such as proteins and peptides. Color bodies and color precursors were removed by NF245 nano filtration. Charcoal treatment with 5% activated carbon removed most of the residual colors to provide a clear solution. After the removal of charcoal by filtration, the clear solution was cooled in a ice bath to 10° C. and acidified with sulfuric acid to provide a white suspension of muconic acid in water. Filtration and drying yielded pure muconic acid as a colorless powder.

Example 3

Synthesis of Dimethyl muconate

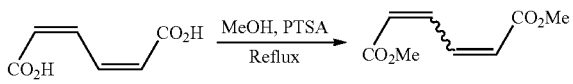

Cis, cis muconic acid (10 g, 70.4 mmol) was suspended in methanol (250 ml). A catalytic amount of p-toluene sulfonic acid (PTSA, 500 mg) was added and the reaction mixture was refluxed for 30 hours. After concentration, the remaining brown residue is taken up in ethyl acetate and extracted 3 times with saturated aqueous $K_2CO_3$. Drying, filtering and evaporation of all solvent results in a light brown solid (10.8 g, 63.5 mmol, 90% yield) consisting mainly of cis,cis and cis,trans dimethyl muconate, which was used in subsequent steps without purification.

Example 4

Synthesis of Muconyl chloride

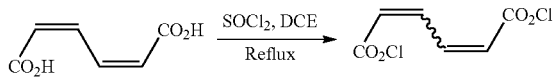

Cis, cis muconic acid (10 g, 70.4 mmol) was suspended in dichloro ethane (DCE, 50 ml). The mixture was brought it to reflux. Thionyl chloride (14.4 ml, 200 mmol) was added slowly over 5 h under relux. The reflux was continued for 12 hours longer after the completion of addition. The reaction mixture was concentrated under vacuum. The remaining brown residue was taken up in ethyl acetate. The brown suspension was stirred at room temperature for 1 hour and filtered to remove solvent and excess acid. A light brown solid (14.8 g) was obtained after drying under vacuum for 2 h at room temperature consisting mainly of cis,cis and cis,trans muconyl chloride, which was used in subsequent steps without purification.

Example 5

Synthesis of Muconic acid Homopolymers

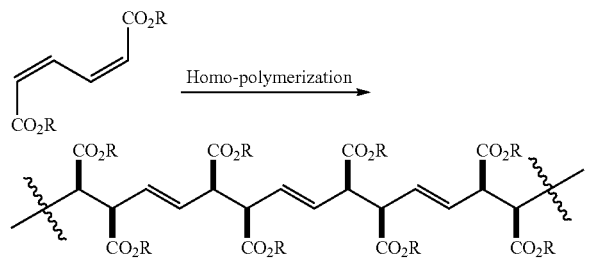

Photo polymerization of the muconic ester crystals is carried out in a sealed Pyrex ampule under irradiation of UV light using a high-pressure mercury lamp at a distance of 10 cm. In a typical polymerization procedure, monomer methyl muconate (EMU, 200 mg, 1 mmol) is placed in an ampule, which is then evacuated on a vacuum line. After irradiation, polymer is isolated by removal of the unreacted monomer with chloroform (20 ml) for 5-6 h at room temperature. Photo polymerization is also carried out by direct exposure to sun light. Post polymerization is performed in a thermo-stated bath in the dark after continuous photo irradiation for a given time.

Example 6

Synthesis of Muconic cross-linking polymer

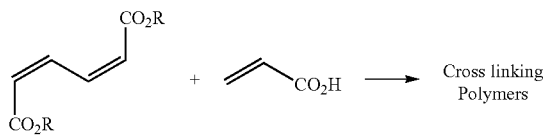

To a brown solid dimethyl mucanate (10 g) is added to acrylic acid (30 ml). The reaction mixture is slowly warmed to 50° C. for over 30 min and left at that temperature for over 3 h. A homogeneous brown reaction mixture is obtained at this point. A small amount of benzoyl peroxide (5 mg) is added to the reaction mixture. The reaction mixture is warmed to 120° C. and kept at that temperature for 4 h. Acrylic acid started to distill at this point. The distilled acrylic acid is collected and the reaction mixture is heated further to 180° C. for over 30 min and left at that temperature for over 3 hours. The resulting mixture is a thick viscous and it is poured over aluminum foil and allowed to cool to room temperature and solidify. The brown solid is the muconic acid cross-linking polymer.

Example 7

Synthesis of Muconic Co-polymer

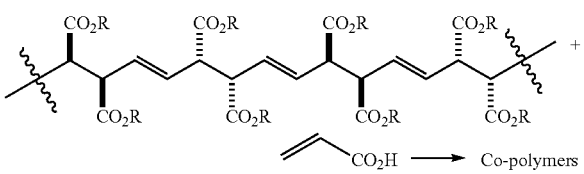

Muconic acid homopolymer is produced as described in Example 5. To a muconic homopolymer (10 g) is added acrylic acid (30 ml). The polymer is instantly dissolved to produce a homogeneous brown reaction mixture. To this reaction mixture is added a catalytic amount of benzoyl peroxide (5 mg). The reaction mixture is warmed to 50° C. over 30 min and left there for 3 h. The reaction mixture is heated further to 120° C. over 30 min and left there for 3 h. Acrylic acid is starting to distill at this point. The distilled acrylic acid is collected. When the distillation stops, the reaction mixture is sealed and heated further to 180° C. and left there for 3 h. The hot, thick and viscous reaction mixture is poured over aluminum foil and allowed to cool to room temperature and solidify. The brown solid is the muconic acid co-polymer.

Example 8

Synthesis of Muconic lactone

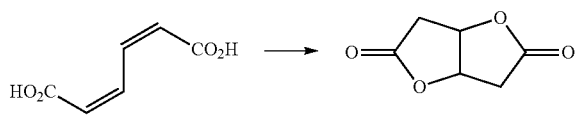

To a solution of THF (100 ml) is added TMSOTf (10 ml) at room temperature under magnetic stirring. To the above reaction mixture is slowly added hexamethyldisilazane (HMDS, 11.8 ml) while keeping the reaction temperature between 25° C. to 35° C. The resulting homogeneous reaction mixture is stirred at room temperature for over 2 h. A colorless muconic acid powder (10 g) is added to the above reaction mixture. The reaction is a suspension and the mixture is warmed to 40° C. and left at that temperature for over 4 h. The reaction mixture slowly became homogeneous and remained homogeneous. After 4 h, 1M HCL solution is added to the reaction mixture. The mixture is agitated vigorously for 30 min. The two phases are separated. The organic phase is washed with water and dried over sodium sulfate and concentrated to provide muconic lactone (8 g).

Example 9

Muconic lactone polymerization

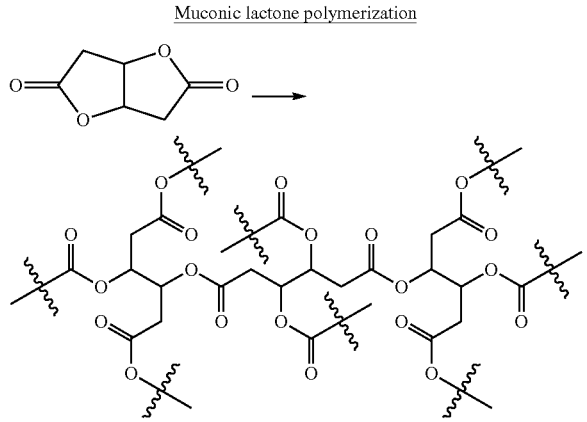

A muconic lactone (10 g) is weighed under argon in a seal tube. The tube is sealed with an air-tight Teflon screw and the edge is further sealed with parafilm and Teflon tape. The tube is heated to 180° C. on a sand bath for over 4 hours. The reaction mixture turned from clear viscous liquid to light brown mixture. The hot, thick and viscous reaction mixture is poured over aluminum foil and allowed to cool to room temperature and solidify. The brown solid is the muconic lactone polymer.

Example 10

Muconic acid polyester

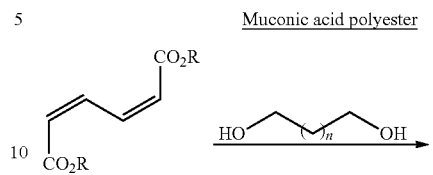

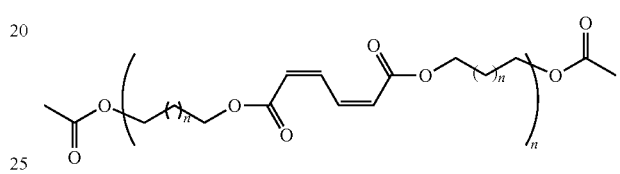

A four necked 100 ml flask is charged with 20 g muconic acid, 18 g 1, 3-propanediol 0.03 g titanium tetraisopropoxide and 0.07 g magnesium hydrogen phosphate trihydrate under dry nitrogen atmosphere. The flask with a gas introduction inlet and outlet connected to a condenser is first immersed in a silicon oil bath preset at 230° C. then heated to remove the esterification byproduct water for 1 hour. Subsequently, the condenser is removed and the polycondensation is carried out over a gradually decreasing pressure for a final vacuum of less than 0.1 mmHg. Polycondensation is considered concluded once the viscosity of the product reaches high enough to twist around stirring rod.

Example 11

Muconic acid polyester co-polymer

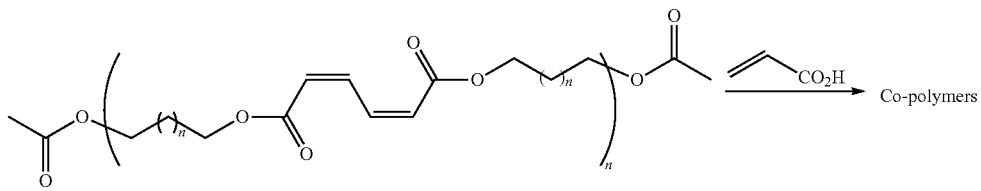

Muconic acid polyester is produced as described in Example 10. To a muconic polyester (10 g) is added acrylic acid (30 ml). The polymer is instantly dissolved to produce a homogeneous clear, colorless reaction mixture. To this reaction mixture is added a catalytic amount of benzoyl peroxide (5 mg). The reaction mixture is warmed to 50° C. over 30 min and left there for 3 h. The reaction mixture is heated further to 120° C. over 30 min and left there for 3 h. Acrylic acid is starting to distill at this point. The distilled acrylic acid is collected. When the distillation stops, the reaction mixture is sealed and heated further to 230° C. and left there for 3 h. The hot, thick and viscous reaction mixture is poured over aluminum foil and allowed to cool to room temperature and solidify. The brown solid is the muconic acid polyester co-polymer.

Example 12

Muconic acid polyamide

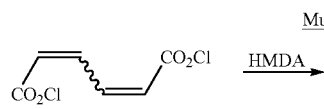

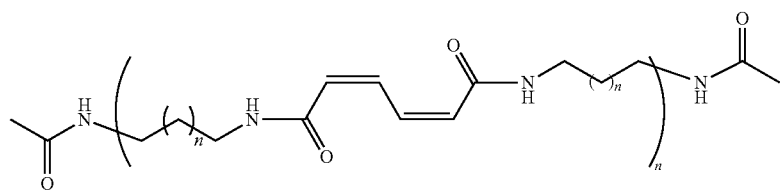

Muconyl chloride is produced as described in Example 4. A solution of muconyl chloride (10 g) in 50 ml cyclohexane is prepared in 250 ml beaker. A 50 ml aqueous solution of 5% HMDA in 5% NaOH is prepared and added slowly through the side of the beaker without agitation. The pH of the aqueous phase is continuously checked, if it is too acidic, a small amount of NaOH is added. A film like polymer is formed between the organic and aqueous phase. An end of a piece of copper wire is bent to a shape of a hook and used to pull the film formed at the interface. When a slow and steady motion is used, a rope of muconic acid polyamide that is several meter long is created. The collected amide is washed with water, dried on a paper towel and weighed it to produce 14 g of muconic acid polyamide.

Example 13

Muconic acid polyamide co-polymer

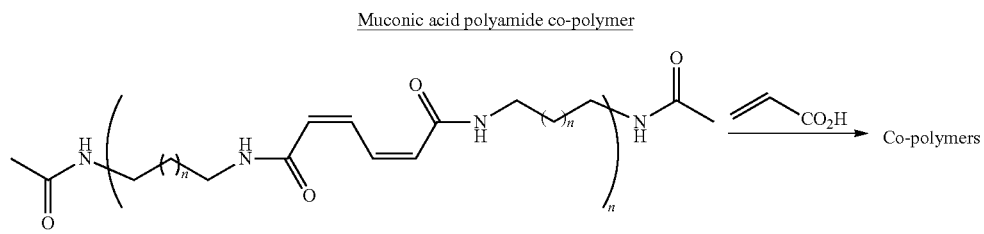

Muconic acid polyamide is produced as described in Example 12. To a muconic polyamide (10 g) is added acrylic acid (30 ml). The polymer is instantly dissolved to produce a homogeneous clear, colorless reaction mixture. To this reaction mixture is added a catalytic amount of benzoyl peroxide (5 mg). The reaction mixture is warmed to 50° C. over 30 min and left there for 3 hours. The reaction mixture is heated further to 120° C. over 30 min and left there for 3 hours. Acrylic acid is starting to distill at this point. The distilled acrylic acid is collected. When the distillation stops, the reaction mixture is sealed and heated further to 230° C. and left there for 3 hours. The hot, thick and viscous reaction mixture is poured over aluminum foil and allowed to cool to room temperature and solidify. The brown solid is the muconic acid polyamide co-polymer.

Example 14

Synthesis of Hex-3-enedioic ester

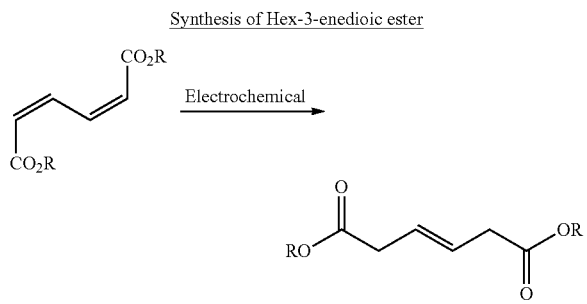

A 50 g diammonium muconate in 500 ml water is used for the electrochemical reaction. A catalytic amount of tetrabutyl ammonium tetrafluroborate (1 g) is added as an electrolyte. A platinum cathode and graphite anode is used for the electrolysis. A heavy duty car battery with 12V and 35 Ah is used for the reaction. The electrochemical reaction is conducted for 4 min and the reaction is analyzed every min after the electrolysis. The complete conversion happened after 6 min to yield hex-3-enedioic acid as a sole product. The aqueous solution is acidified with sulfuric acid and extracted with ethyl acetate, concentrated and dried to produce hex-3-enedioic ester (28 g) as a colorless viscous liquid.

Example 15

Synthesis of 2, 5 dimethylene-3-enedioic ester

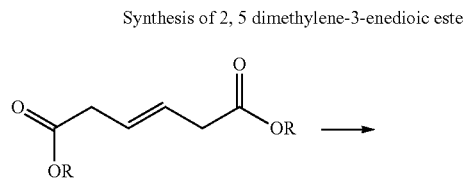

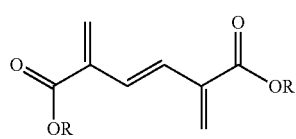

Hex-3-enedioic ester is produced as described in Example 14. To a solution of 10 g hex-3-enedioic ester in 30 ml water is added 30 ml of 30% formaldehyde solution in water. To the reaction mixture is added 10 ml 1M solution of NaOH. The reaction mixture is heated to 80° C. over 30 min and left at that temperature for 12 hours. The resulting reaction mixture is concentrated under vacuum to a total volume of 20 ml. The reaction mixture is cooled under ice to 10° C. and acidified with sulfuric acid to pH 1.0. A white precipitate of 2, 5 dimethylene-3-enedioic ester is immediately appeared. The precipitate is filtered and dried to yield 4.8 g of 2, 5 dimethylene-3-enedioic ester.

Example 16

2, 5 dimethylene-3-enedioic ester cyclization

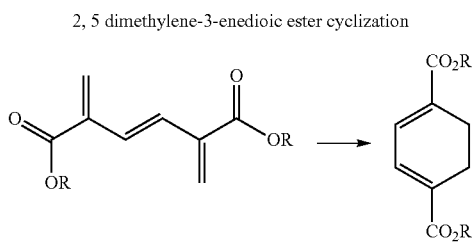

2, 5 dimethylene-3-enedioic ester is produced as described in Example 15. To a solution of 2, 5 dimethylene-3-enedioic ester (10 g) in THF (60 ml) is added catalytic amount (200 mg) of $SnCl_4$. The reaction mixture turned light brown immediately. The brown mixture is refluxed under nitrogen for 12 hours. The reaction mixture is quenched with 10% $Na_2CO_3$ solution. The organic layer is washed with water, dried under sodium sulfate and concentrated to produce brown solid (6.8 g) as a product. The product is directly used for the subsequent steps without further purifications.

Example 17

Oxidation of dihydroterephthalic acid

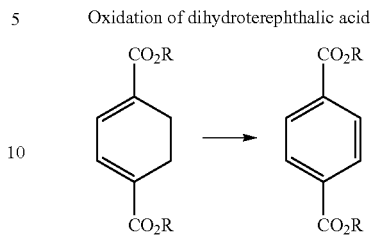

Cyclization reaction product as produced above in Example 16 is dissolved in 60 ml THF. A catalytic amount of 10% Rh/C (10 mg) is added to the reaction. The reaction mixture is transferred to the high pressure hydrogenation reactor. And heated to 120° C. under high pressure. The reaction mixture is analyzed for product formation every 1 hour. The reaction is completed after 6 hours at 120° C. The reaction mixture is filtered to remove Rh/C and evaporated to remove THF to produce terephthalic ester as a thick paste.

Example 18

Hydroenation reaction

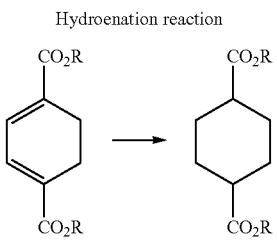

Cyclization reaction product as produced above in Example 16 is dissolved in 60 ml THF. A catalytic amount of 5% Pd/C (20 mg) is added to the reaction mixture. The reaction mixture is transferred to the high pressure hydrogenation reactor. The reaction mixture is vacuum displaced with hydrogen gas to 20 psi hydrogen pressure. The reaction mixture is heated to 80° C. and left at that temperature for 1 h. The reaction is completed after 1 hour at 80° C. The reaction mixture is filtered to remove Pd/C and evaporated to remove THF to produce cyclohexane dicarboxylic ester as a thick paste.

Example 19

Synthesis of 3,4 disulfohexanedioic acid

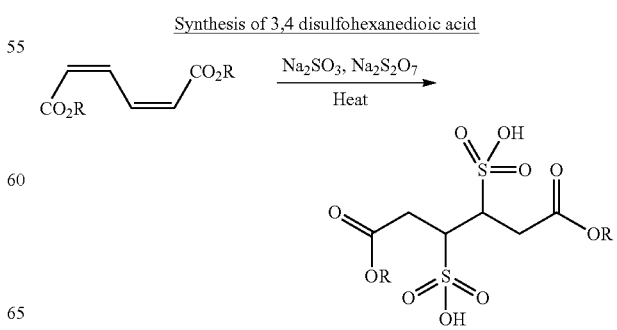

To a suspension of 10 g muconic acid in 60 ml distilled water was added 24 g sodium sulfite and 6 g sodium thio sulfate. The suspension dissolved immediately to form a clear solution. The homogeneous solution was heated to 80° C. and left at that temperature for over 36 hours. The reaction mixture was analyzed by HPLC for the consumption of starting material. Complete consumption is observed in 30 hours. The reaction mixture was concentrated to dryness, dissolved in ethanol and added concentrated HCl. The precipitated NaCl salt was filtered off and ethanol/water mixture was evaporated to dryness to provide pure 3,4 disulfohexanedioic acid. The resulting product is directly used for the subsequent polymerization reactions.

Example 20

Synthesis of 2,3,4,5 tetrabromohexanedioic acid

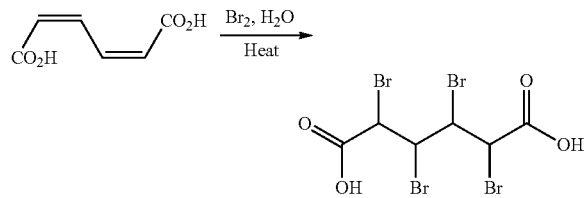

A suspension of 10 g muconic acid in 50 ml distilled water was heated to 90° C. The suspension turned to a clear homogeneous solution. 16 ml bromine solution was added dropwise to the hot reaction mixture. The reaction mixture turned to deep red in color and red color 2,3,4,5 tetrabromohexanedioic acid solid started to appear. The reaction was continued till all the bromine and muconic acid was consumed. The hot reaction mixture was filtered hot to leave the impurities in the water. Pale yellow 2,3,4,5 tetrabromohexanedioic acid was washed with hot water and dried in vacuum oven for 8 h to provide 18 g pure 2,3,4,5 tetrabromohexanedioic acid. The resulting product is suitable for further use in polymerization reactions.

REFERENCES

All references are listed for the convenience of the reader. Each reference is incorporated by reference in its entirety
U.S. Pat. No. 3,429,949
U.S. Pat. No. 3,497,479
U.S. Pat. No. 3,562,209
U.S. Pat. No. 3,615,434
U.S. Pat. No. 3,671,572
U.S. Pat. No. 3,919,142
U.S. Pat. No. 3,914,195
U.S. Pat. No. 4,031,136
U.S. Pat. No. 4,393,196
U.S. Pat. No. 4,401,795
U.S. Pat. No. 4,461,887
U.S. Pat. No. 4,480,034
U.S. Pat. No. 4,535,059
U.S. Pat. No. 4,588,688
U.S. Pat. No. 4,608,338
U.S. Pat. No. 4,661,588
U.S. Pat. No. 4,681,852
U.S. Pat. No. 4,753,883
U.S. Pat. No. 4,833,078
U.S. Pat. No. 4,968,612
U.S. Pat. No. 5,168,056
U.S. Pat. No. 5,272,073
U.S. Pat. No. 5,487,987
U.S. Pat. No. 5,616,496
U.S. Pat. No. 6,600,077
U.S. Pat. No. 6,180,373
U.S. Pat. No. 6,210,937
U.S. Pat. No. 6,472,169
U.S. Pat. No. 6,613,552
U.S. Pat. No. 6,962,794
U.S. Pat. No. 7,244,593
U.S. Pat. No. 7,388,064
U.S. Pat. No. 7,638,312
U.S. Pat. No. 7,790,431
U.S. Pat. No. 7,880,030
U.S. Pat. No. 8,367,858
U.S. Pat. No. 8,367,859
U.S. Pat. No. 8,415,496
U.S. Pat. No. 8,426,639
U.S. Pat. No. 8,742,060
U.S. Pat. No. 8,809,583
U.S. Pat. No. 8,829,237
U.S. Pat. No. 8,895,779
U.S. Pat. No. 8,946,472
US Patent Application Publication No. US 2009/0191610
U.S. Patent Application Publication No. US 2010/0314243 A
U.S. Patent Application Publication No. US 2011/0288263 A1
U.S. Patent Application Publication No. US 2013/0085255 A1
U.S. Patent Application Publication No. US 2013/0085747 A1
U.S. Patent Application Publication No. US 2014/0171614 A1
U.S. Patent Application Publication No. US 2015/0225329 A1
U.S. Patent Application Publication No. US 2014/0171614 A1
U.S. Patent Application Publication No. US 2014/0228595 A1
U.S. Patent Application Publication No. US 20140302573 A1
U.S. Patent Application Publication No. US 2015/0203880
European Patent Application No. 86300748.0
International Patent Application Publication No. WO 90/10654
International Patent Application Publication No. WO 2011/017560
International Patent Application Publication No. WO 2011/085311
International Patent Application Publication No. WO 2011/123154
International Patent Application Publication No. WO 2013/085747
International Patent Application Publication No. WO 2013/109865
International Patent Application Publication No. WO 2013/116244
International Patent Application Publication No. WO 2014/047407
International Patent Application Publication No. WO 2014/102280
International Patent Application Publication No. WO 2015/069847
International Patent Application Publication No. WO 2015/086827

Averesch, N. J. H. and Kromer, J. O. (2014) Tailoring strain construction strategies for muconic acid production in *S. cerevisiae* and *E. coli*. *Metabol. Engineer. Comm.* 1, 19-28.

Chiba, T., Okimoto, M., Nagai, H. and Takata, Y. (1983) Electrocatalytic reduction using raney nickel. *Bull. Chem. Soc. Jpn.* 56, 719-723.

Choi, W. J., Lee, E. Y., Cho, M. H., and Choi, C. Y. (1997) Enhanced production of cis, cis-muconate in a cell-recycle bioreactor. *J. Fermentation and Bioengineering.* 84, 70-76.

Curran, K. A., Leavitt, J. M., Karim, A. S. and Alper, H. S. (2012) Metabolic engineering of muconic acid production in *Saccharomyces cerevisiae*. *Metabol. Engineer.* 15, 55-66.

Kaneko, A., Ishii, Y., and Kirimura, K. (2011) High-yield production of cis, cis-muconic acid from catechol in aqueous solution by biocatalyst. *Chem. Lett.* 40, 381-383.

Matsumoto, A. (2003) Polymer structure control based on crystal engineering for materials design. *Polymer J.* 35, 93-121.

Matsumoto, A., Fujioka, D. and Kunisue, T. (2003) Organic intercalation of unsaturated amines into layers polymer crystals and solid-state photoreactivity of the guest molecules in constrained interlayers. *Polymer J.* 35, 652-661.

Mizuno, S., Yoshikawa, N., Seki, M., Mikawa, T., and Imada, Y. (1988) Microbial production of cis, cis-muconic acid from benzoic acid. *Appl Microbiol Biotechnol.* 28, 20-25.

Niu, W., Draths, K. M., and Frost, J. W. (2002) Benzene-free synthesis of adipic acid, *Biotechnol Prog* 18, 201-211.

Odani, T. and Matsumoto, A. (2002) Solvent-free synthesis of layered polymer crystals. *Polymer J.* 34, 841-846.

Perez-Pantoja, D., De la Iglesia, R., Pieper, D. H., and Gonzalez, B. (2008) Metabolic reconstruction of aromatic compounds degradation from the genome of the amazing pollutant-degrading bacterium *Cupriavidus necator* JMP134, *FEMS Microbiol Rev* 32, 736-794.

Perez-Pantoja, D., Donoso, R., Agullo, L., Cordova, M., Seeger, M., Pieper, D. H., and Gonzalez, B. (2011) Genomic analysis of the potential for aromatic compounds biodegradation in Burkholderiales, *Environ Microbiol*.

Sun, X., Lin, Y., Huang, Q., Yuan, Q. and Yan, Y. (2013) A novel muconic acid biosynthesis approach by shunting tryptophan biosynthesis via anthranilate. *App. Environ. Micorbiol.* 79, 4024-4030.

Weber, C., Bruckner, C., Weinreb, S., Lehr, C., Essl, C. and Bole, E. (2012) Biosynthesis of cis, cis-muconic acid and its aromatic precursors catechol and proteocatechuic acid, from renewable feedstocks by *Saccharomyces cerevisiae, App Environ Microbiol.* 78, 8421-8430.

Xie, N.-Z., Lilang, H., Huang, R-B. and Xu, P. (2014) Biotechnological production of muconic acid: current status and future prospects. *Biotech. Adv.* 32, 615-622.

Yoshikawa, N., Mizuno, S., Ohta, K., and Suzuki, M. (1990) Microbial production of cis, cis-muconic acid. *J. Biotechnol.* 14, 203-210.

Zhang, H., Li, Z., Pereira, B. and Stephanopoulos (2015) Engineering *E. coli-E. coli* cocultures for production of muconic acid from glycerol. *Microb. Cell Fact.* 14, 134-143.

Zhang, H., Pereira, B., Li, Z. and Stephanopoulos (2015) Engineering *Escherichia coli* coculture system for the production of biochemical products. *Proc. Natl. Acad. Sci. USA* 112, 8266-8271.

What is claimed:

1. A method for making a polymer from muconic acid, the method comprising:
    (a) obtaining muconic acid from a microorganism;
    (b) optionally converting the muconic acid to a muconic acid derivative of the following formula (I)

$$RO_2C—CH=CH—CH=CH—CO_2R \qquad (I)$$

wherein R is selected from the group consisting of an alkyl group, an aryl group, an alkyl aromatic group, and an aromatic alkyl group; and
    (c) reacting the muconic acid or the muconic acid derivative via an electrochemical reaction, to obtain hex-3-enedioic acid or an alkyl, aryl, alkyl aromatic or aromatic alkyl ester of hex-3-enedioic acid,
    (d) condensing the hex-3-enedioic acid or the alkyl, aryl, alkyl aromatic or aromatic alkyl ester of hex-3-enedioic acid with an aldehyde or ketone, and
    (e) reacting a product of (d), to obtain the polymer.

2. The method of claim 1, wherein R is $CH_3$.

3. The method of claim 1, wherein R is $C_2H_5$.

4. The method of claim 1, wherein the microorganism is a bacterium.

* * * * *